(12) United States Patent
Bonutti

(10) Patent No.: US 10,709,944 B2
(45) Date of Patent: Jul. 14, 2020

(54) DEVICES, SYSTEMS, AND METHODS

(71) Applicant: P Tech, LLC, Effingham, IL (US)

(72) Inventor: Peter M. Bonutti, Manalapan, FL (US)

(73) Assignee: P Tech, LLC, Effingham, IL (US)

( * ) Notice: Subject to any disclaimer, the term of this patent is extended or adjusted under 35 U.S.C. 154(b) by 145 days.

(21) Appl. No.: 15/908,270

(22) Filed: Feb. 28, 2018

(65) Prior Publication Data

US 2018/0243626 A1    Aug. 30, 2018

Related U.S. Application Data

(60) Provisional application No. 62/464,704, filed on Feb. 28, 2017.

(51) Int. Cl.
*A61B 34/00* (2016.01)
*A61N 1/36* (2006.01)
(Continued)

(52) U.S. Cl.
CPC ............. *A63B 60/12* (2015.10); *A42B 3/125* (2013.01); *A61B 5/0488* (2013.01); *A61B 34/74* (2016.02); *A61B 34/76* (2016.02); *A61L 2/10* (2013.01); *A61L 2/22* (2013.01); *A61N 1/3603* (2017.08); *A61N 1/36003* (2013.01); *A63B 24/0003* (2013.01); *A63B 49/02* (2013.01); *A63B 49/08* (2013.01); *A63B 51/00* (2013.01);
(Continued)

(58) Field of Classification Search
CPC ......... A63B 60/12; A63B 53/10; A63B 34/74; A63B 60/14; A63B 49/08; A63B 71/141; A63B 34/76; A63B 60/46; A63B 24/0003; A63B 2053/0445; A63B 2071/0655; A63B 2060/0081; A63B 2034/741; A63B 2230/00; A63B 2090/064; A63B 2225/50; A63B 2220/80; A63B 5/04888; A63B 5/0408; A63B 5/0488; A61L 2/22; A61L 2/10; A61N 1/36; A61N 1/36003; A61N 1/3603
See application file for complete search history.

(56) References Cited

U.S. PATENT DOCUMENTS

2004/0082979 A1* 4/2004 Tong .................... A61N 1/0452
607/48
2012/0101595 A1* 4/2012 Jung ........................ A61F 2/68
623/25
(Continued)

OTHER PUBLICATIONS

International Search Report and Written Opinion for application PCT/US2018/020243 dated May 7, 2018, 12 pages.

*Primary Examiner* — Catherine M Voorhees
(74) *Attorney, Agent, or Firm* — Stinson LLP

(57) ABSTRACT

Devices systems and methods are disclosed. Among other things, the devices systems and methods can facilitate ergonomic gripping of a handle; conform to the shape of a wrist; enhance golf techniques or performance; enhance racket sport technique or performance; protect a head of a user engaged in contact sports or other hazardous activities; identify concussions, in some cases in substantially real time; provide sterilization of garments; control surgical robots; allow for medical treatment of multiple subjects without disrobing; provide biometric or other data; and/or be used to train muscles or body parts for, for example, performing specified tasks using a body part.

18 Claims, 41 Drawing Sheets

(51) Int. Cl.

| | | |
|---|---|---|
| *A61B 5/0488* | (2006.01) | |
| *A63B 60/12* | (2015.01) | |
| *A63B 24/00* | (2006.01) | |
| *A63B 53/04* | (2015.01) | |
| *A63B 53/14* | (2015.01) | |
| *A63B 60/46* | (2015.01) | |
| *A63B 71/14* | (2006.01) | |
| *A42B 3/12* | (2006.01) | |
| *A63B 69/36* | (2006.01) | |
| *A63B 49/02* | (2015.01) | |
| *A63B 51/08* | (2006.01) | |
| *A63B 49/08* | (2015.01) | |
| *A63B 60/14* | (2015.01) | |
| *A63B 51/00* | (2015.01) | |
| *A63B 53/10* | (2015.01) | |
| *A61L 2/10* | (2006.01) | |
| *A61L 2/22* | (2006.01) | |
| *A63B 60/04* | (2015.01) | |
| *A63B 60/02* | (2015.01) | |
| *A61B 90/00* | (2016.01) | |
| *A63B 60/00* | (2015.01) | |
| *A63B 71/06* | (2006.01) | |
| *A61B 34/30* | (2016.01) | |

(52) U.S. Cl.
CPC .............. *A63B 51/08* (2013.01); *A63B 53/04* (2013.01); *A63B 53/10* (2013.01); *A63B 53/14* (2013.01); *A63B 60/14* (2015.10); *A63B 60/46* (2015.10); *A63B 69/36* (2013.01); *A63B 71/141* (2013.01); *A63B 71/146* (2013.01); *A61B 34/30* (2016.02); *A61B 2034/741* (2016.02); *A61B 2090/064* (2016.02); *A61L 2202/11* (2013.01); *A61L 2202/14* (2013.01); *A61L 2202/15* (2013.01); *A61L 2202/26* (2013.01); *A63B 60/02* (2015.10); *A63B 60/04* (2015.10); *A63B 2051/004* (2013.01); *A63B 2053/0433* (2013.01); *A63B 2053/0445* (2013.01); *A63B 2053/0458* (2013.01); *A63B 2053/0491* (2013.01); *A63B 2060/0081* (2015.10); *A63B 2071/0655* (2013.01); *A63B 2220/51* (2013.01); *A63B 2220/70* (2013.01); *A63B 2220/80* (2013.01); *A63B 2225/09* (2013.01); *A63B 2225/50* (2013.01); *A63B 2230/00* (2013.01)

(56) References Cited

U.S. PATENT DOCUMENTS

| | | | |
|---|---|---|---|
| 2014/0058476 A1 | 2/2014 | Crosby et al. | |
| 2014/0128939 A1* | 5/2014 | Embrey | A61N 1/36003 607/49 |
| 2015/0364052 A1* | 12/2015 | Blankenship | G09B 5/00 434/11 |
| 2016/0106994 A1* | 4/2016 | Crosby | A61N 1/36135 600/13 |

* cited by examiner

DEVICES, SYSTEMS, AND METHODS

CROSS-REFERENCE TO RELATED APPLICATIONS

This application claims priority to U.S. Provisional Patent Application Ser. No. 62/464,704, filed on Feb. 28, 2017 and entitled DEVICES, SYSTEMS, AND METHODS, which is hereby incorporated by reference in its entirety.

FIELD

This disclosure generally pertains to devices systems and methods for, among other things, facilitating grip of a handle, conforming to the shape of a wrist, enhancing golf techniques/performance, enhancing racket sport technique/performance, protecting a head, identifying concussions, sterilization, and/or muscle training.

BACKGROUND

Sporting equipment such as baseball bats, tennis rackets, golf clubs, cricket bats, etc. are configured to be held in the hand of user and typically have substantially constant cross-sectional shapes along their lengths.

Fitness tracking devices and other biometric analyzers are often worn on a user's wrists. Typically, analyzers are attached to a user's wrists using a strap that extends circumferentially around the user's wrist and includes a clasp or fastener for securing one end to the other.

Golf clubs typically comprise a head having a predetermined weight that is fixedly mounted to the end of a shaft. A conventional head has a substantially rigid face defining a plurality of horizontal grooves and a smooth sole for gliding over the ground with low frictional resistance.

Tennis rackets include a fixed weight frame mounted on a handle and strings arranged to extend along a plurality of equally spaced vertical segments and a plurality of equally spaced horizontal segments.

Sports helmets typically comprise a rigid exoskeleton or shell.

Various concussion protocols are used by sports leagues to evaluate players for concussions after head trauma incidents. These tests are oftentimes performed on the sidelines of a game, between spectators and game play in action.

Physical activity requires proper muscular activation sequencing. For example, high performing athletes activate and relax muscles in consistent sequences to carry out repetitive motions for various techniques within their sports. In addition, lay people activate and relax muscles in normal sequences to carry out mundane motions such as walking, running, etc.

Gloves and other disposable medical garments are often thrown away or disrobed for sterilization after a single procedure or contact with a single patient.

SUMMARY

In one aspect, a handgrip for positioning fingers of a hand of a user in a desired configuration when grasping a handle comprises a spacer for being received between the hand of the user and the handle and having a top surface for engaging the hand of the user, a bottom surface for engaging the handle, a first end, a second end, a thickness extending from the top surface to the bottom surface, and length extending from the first end to the second end. The length of the spacer includes a first hand-engaging segment and a second hand-engaging segment. The top surface is configured to engage the hand at a location aligned with a first one of the fingers of the user along the first hand-engaging segment and at a location aligned with a second one of the fingers of the user along the second hand-engaging segment. The thickness of the spacer along the first hand-engaging segment is larger than the thickness of the spacer along the second hand-engaging segment. A strap is connected to the spacer and configured to secure the spacer to the hand of the user such that the top surface is engaged with the hand, the first hand-engaging segment is aligned with the first finger, and the second hand-engaging segment is aligned with the second finger.

In an embodiment of the hand grip, the top surface is contoured to the first finger along the first hand-engaging segment.

In another embodiment of the hand grip, the bottom surface is contoured to the handle.

In another aspect, a kit for positioning fingers of a user in a desired configuration when grasping a handle comprises a first spacer for being received between a first finger of the user and the handle and having a first thickness. A second spacer is configured for being received between a second finger of the user and the handle and has a second thickness. A first strap is configured for securing the first spacer to the first finger. A second strap is configured for securing the second spacer to the second finger.

In yet another aspect, a glove for positioning fingers of a user in a desired configuration when grasping a handle comprises a shell including a first finger receptacle for receiving a first finger of the user therein and a second finger receptacle for receiving a second finger of the user therein. A first spacer is attached to the first finger receptacle for being received between the first finger and the handle and has a first thickness. A second spacer is attached to the second finger receptacle for being received between the second finger and the handle and has a second thickness.

In still another aspect, a handle for a sports implement comprises a first end, a second end, and length extending from the first end to the second end. The handle includes a first hand-engaging spacer extending along a first segment of the length for supporting a portion of the hand grasping the handle aligned with a first finger of the hand, a second hand-engaging spacer extending along a second segment of the length for supporting a portion of the hand aligned with a second finger of the hand grasping the handle, and a third hand-engaging spacer extending along a third segment of the length for supporting a portion of the hand aligned with a third finger of the hand grasping the handle. The first, second, and third supports are shaped and arranged to align tips of the first, second, and third fingers along a grip axis when the hand grasps the handle.

In another aspect, an adjustable handle for a sports implement comprises a shaft having an axis and a handgrip mounted on the shaft. The handgrip comprises a first hand-engaging member mounted on the shaft for rotation with respect to the shaft about the axis. The first hand-engaging member has a perimeter surface extending circumferentially around the axis. The perimeter surface has a radial position with respect to the axis that varies as the perimeter surface extends circumferentially around the axis. A second hand-engaging member is mounted on the shaft at a location spaced apart from the first hand-engaging member along the axis for selective rotation with respect to the shaft about the axis. The first hand-engaging member has a perimeter surface extending circumferentially around the axis. The perimeter surface of the second hand-engaging member has a radial position with respect to the axis that varies as the perimeter surface extends circumferentially around the axis.

In yet another embodiment, a handle for a sports implement comprises a shaft having an axis. A handgrip is mounted on the shaft for selective rotation about the axis through a range of motion having a first position and a second position. The handgrip has a first end, a second end, and a length extending along the axis from the first end to the second end. The handgrip includes a first hand-engaging spacer extending along a first segment of the length for supporting a portion of the hand grasping the handle aligned with a first finger of the hand and a second hand-engaging spacer extending along a second segment of the length for supporting a portion of the hand aligned with a second finger of the hand grasping the handle to align the first and second fingers in a desired configuration when the hand grasps the handle. The handgrip is configured to position the hand of the user in a first grip position of the sports implement when the handgrip is rotated to the first position and in a second grip position of the sports implement when the handgrip is rotated to the second position.

In still another aspect, an adjustable golf club handle comprises a shaft having an axis. A first handgrip for being grasped by a first hand of a golfer is mounted on the shaft. A second handgrip for being grasped by a second hand of the golfer is mounted on the shaft at a spaced apart position from the first handgrip along the axis and has a perimeter extending circumferentially around the axis and including an indicator formation extending along the axis that provides a tactile indication to the golfer of the circumferential position of the second hand with respect to the second handgrip when the second hand grasps the second handgrip. The second handgrip is selectively rotatable about the axis with respect to the shaft and the first handgrip.

In an embodiment of the adjustable golf club, the first handgrip has a perimeter extending circumferentially around the axis and includes an indicator formation extending along the axis that provides a tactile indication to the golfer of the circumferential position of the first hand with respect to the first handgrip when the first hand grasps the first handgrip. The first handgrip is selectively rotatable about the axis with respect to the shaft and the second handgrip.

In another aspect, a wristband for supporting a device on a wrist of a user having a radius side portion and an ulna side portion comprises a top segment having a first end and a second end. A radius side segment for conformingly engaging the radius side portion of the wrist of the user extends from the first end of the top segment and an ulna side segment for conformingly engaging the ulna side portion of the wrist of the user extends from the second end of the top segment.

In yet another aspect, an adjustable golf club comprises a shaft having a proximal end and a distal end spaced apart along a center axis. A club head extends from the distal end of the shaft and is attached to the shaft at a joint region adjacent the distal end of the shaft. An eccentric weight is mounted on the shaft adjacent the joint region for rotation about the center axis of the shaft and has a center of mass that is radially offset from the center axis of the shaft.

In still another aspect, a golf club comprises a shaft having a proximal end and a distal end. A club head is mounted on the distal end of the shaft and has a face for striking a golf ball supported on a ground region and a sole for engaging the ground region as the golf club is swung to strike the golf ball. The sole defines a traction formation for creating enhanced friction between the sole and the ground region as the golf club is swung to reduce a speed of the golf club as the golf club strikes the golf ball.

In another aspect, a club head for a golf club comprises a face, a back, and a thickness extending between the face and the back. The club head defines a plurality of holes spaced apart along the face and extending through at least a portion of the thickness.

In an embodiment of the club head, the club head comprises a metal. The club head further comprises polymer plugs at least partially filling at least some of the plurality of holes.

In another embodiment of the club head, the club head has a sweet spot region and a perimeter region extending circumferentially around the sweet spot region. The thickness is smaller through the sweet spot region than the perimeter region.

In still another embodiment of the club head, the holes are formed in the sweet spot region.

In another aspect, a club head for a golf club comprises a face having a top end margin and a bottom end margin and a sole extending rearward from the bottom end margin of the face and extending laterally, generally along a sole line. The club head has a plurality of elongate grooves. At least some of the elongate grooves are oriented transverse to the sole line.

In yet another aspect, a shaft for a golf club has a proximal end, a distal end, and a length extending along a shaft axis from the proximal end to the distal end. The shaft includes a main segment extending distally along the shaft axis from the proximal end to a distal end of the main segment and has a cross-sectional shape in a plane orthogonal to the shaft axis that is substantially round. The shaft further includes a flex control segment that extends distally along the shaft axis from adjacent the distal end of the main segment toward the distal end of the shaft and has a cross-sectional shape in a plane orthogonal to the shaft axis that includes a flat side.

In another aspect, a racket comprises a handle having an axis. A head having a perimeter is mounted on the handle and defines a plurality of string holes configured to receive one or more strings strung onto the racket. The string is woven to define at least one of the following types of string segments: (a) skewed segments of extending along at least one skew axis oriented at a skew angle with respect to the axis of the handle; and (b) unequally spaced segments extending along an unequally spaced string axis at spaced apart positions along a spacing axis such that each adjacent pair of the unequally spaced segments is spaced apart by a spacing distance and at least one spacing distance is larger than others of the spacing distances.

In still another aspect, an adjustable racket comprises a frame and at least one balancing weight selectively securable to the frame at any of a plurality of spaced apart locations along the frame.

In yet another aspect, a racket comprises a frame having a head. One or more strings is strung onto the frame to define a plurality string segments along the head. Some of the string segments of the head are strung to have greater tension than others of the string segments.

In another aspect, a helmet comprises a rigid skeleton having an exterior side and an interior side defining a cavity for receiving a head of a user. Deformable padding is formed over the exterior side of the skeleton.

In still another aspect, a system for evaluating whether a person has sustained a concussion comprises a headset configured to be worn by the person and to limit at least one of an environmental acoustic stimulus and an environmental optical stimulus conveyed to the person when the headset is worn by the person. At least one concussion diagnostic transmitter is mounted on the headset for transmitting a diagnostic signal to the person. The at least one concussion diagnostic transmitter is selected from a group of concussion diagnostic transmitters consisting of an acoustic transmitter mounted on the headset to transmit acoustic signals to the ears of the person when the headset is worn by the person and an optical transmitter mounted on the headset to transmit optical signals to the eyes of the person when the headset is worn by the person. A cognitive response sensor is mounted on the headset for sensing a cognitive response of the person to the diagnostic signal and transmitting a cognitive response signal representative of the sensed cognitive response. A cognitive response analyzer is operatively connected to the cognitive response sensor to receive the cognitive response signal and to analyze the cognitive response signal to determine whether the person has sustained a concussion.

In yet another aspect, a method of treating multiple subjects comprises donning a UV-opaque sterile garment. A first patient is contacted with the sterile donned garment to treat the first patient, thereby desterilizing the garment, The donned desterilized garment is re-sterlized without disrobing by inserting the donned desterilized garment into a sterilization chamber and directing UVC light to the donned garment in the sterilization chamber. A second patient is contacted with the re-sterilized donned garment to treat the second patient.

In another aspect, a garment for being donned by a practitioner while treating multiple patients comprises a body defining a cavity having an enclosed perimeter portion for receiving a body part of the practitioner. The body has at least one layer extending around substantially the entire enclosed perimeter portion of the cavity that is UV opaque, and the body has at least one layer extending around the entire enclosed perimeter portion of the cavity that is non-porous.

In one embodiment of the garment, the garment comprises a glove.

In another aspect, a muscle activation system comprises a stimulation generator configured to generate a muscle activation stimulus. A plurality of stimulation transmitters are operatively connected to the stimulation generator and configured to transmit the muscle activation stimulus from the stimulation generator to respective muscles of a subject. A controller is configured to sequence the transmission of the muscle activation stimulus through each of the stimulation transmitters to each of the respective muscles.

In still another aspect, a method of training a body part comprises coupling a muscle activation stimulus generator to the body part. A muscle activation stimulus is generated using the generator. The generated muscle activation stimulus is transmitted to a muscle of the body part to activate the muscle.

In yet another aspect, a muscle activation system comprises a stimulation generator configured to generate a muscle activation stimulus. A plurality of stimulation transmitters are operatively connected to the stimulation generator and configured to transmit the muscle activation stimulus from the stimulation generator to respective muscles of a subject. A controller is configured to control the generator to generate a predefined sequence of muscle activation stimuli. The stimulation transmitters are configured to transmit the predefined sequence of muscle activation stimuli that is generated by the stimulation generator to the respective muscles of the subject to activate the respective muscles of the subject in a muscle activation sequence that causes a body part of the subject to perform a specified movement.

Other aspects, features, and embodiments will also be apparent hereinafter.

BRIEF DESCRIPTION OF THE DRAWINGS

Corresponding reference numbers indicate corresponding parts throughout the drawings.

DETAILED DESCRIPTION

Figure 1:
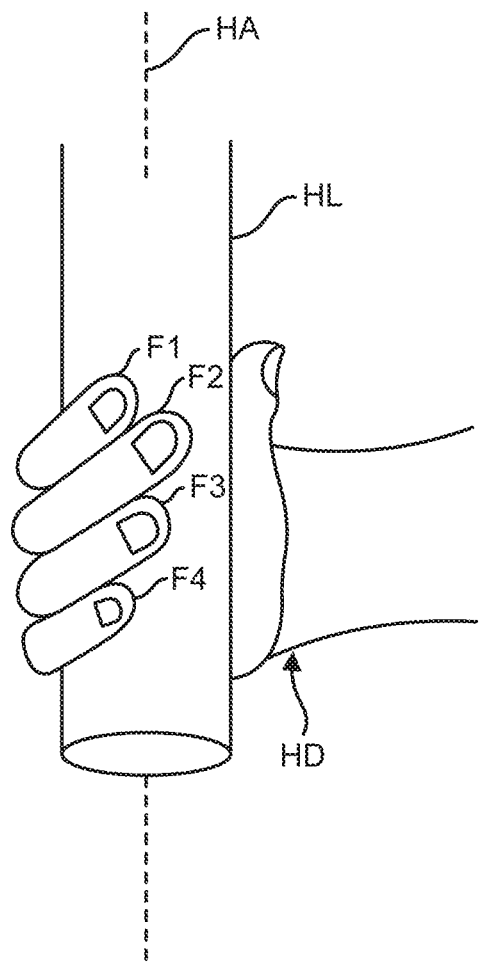
FIG. 1 is a schematic illustration of a hand gripping a conventional handle of the prior art.

During gameplay in many sports, such as tennis, golf, baseball, softball, hockey, badminton, lacrosse, rowing, and cricket, an individual grips the handle of a sporting implement, such as a tennis racket, golf club, baseball bat, softball bat, hockey stick, badminton racket, lacrosse stick, oar, cricket bat, etc. Likewise, various occupational tasks, such as surgery, construction, cooking, military training/battle, etc., require gripping the handle of implements such as surgical instruments, hammers, drivers, drills, pots, spoons, spatulas, firearms, hand combat weapons, etc. As shown in FIG. 1, such handles HL typically extend along a handle axis HA and have substantially constant cross-sectional shapes along their lengths. As a result, conventional implement handles HL are not shaped to account for the unique anatomical details of the human hand HD. When the hand HD grasps the handle HL, the fingers F1-F4 curl around a portion of the outer perimeter of the handle. But each finger F1-F4 has a different length, and the locations of the joints of each finger are not aligned on any common axis. When the fingers F1-F4 bend to curl around an object such as a handle, each finger has a different nominal radius of curvature that is a function of the length and joint locations of the finger. Due to the differences in nominal radius of curvature, in normal grip positions, the ends or tips of the fingers F1-F4 are not aligned with one another, which causes uneven pressure (e.g., counter-pressure) to be applied to each of the fingers. The pinky finger F4 has the smallest nominal radius of curvature of the fingers F1-F4, and therefore, applies a disproportionately large amount of power and stabilization forces to the handle HL and receives a disproportionately large amount of pressure when the hand HD maneuvers the handle in use. Because the pinky finger F4 is also the thinnest and weakest finger of the hand HD, control and power when maneuvering the handle HL is diminished.

Figure 2:
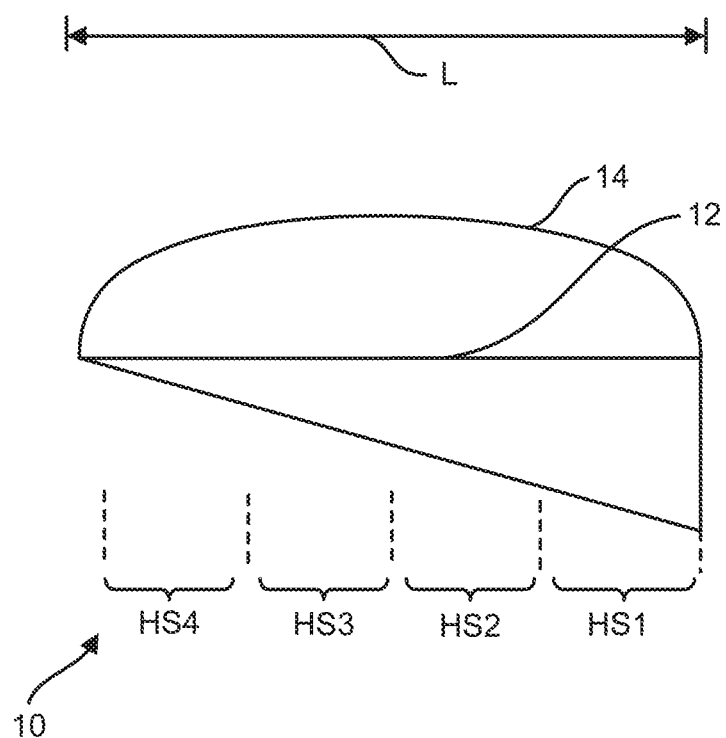
FIG. 2 is a schematic illustration of a handgrip for supporting the hand on the handle.
Figure 3:
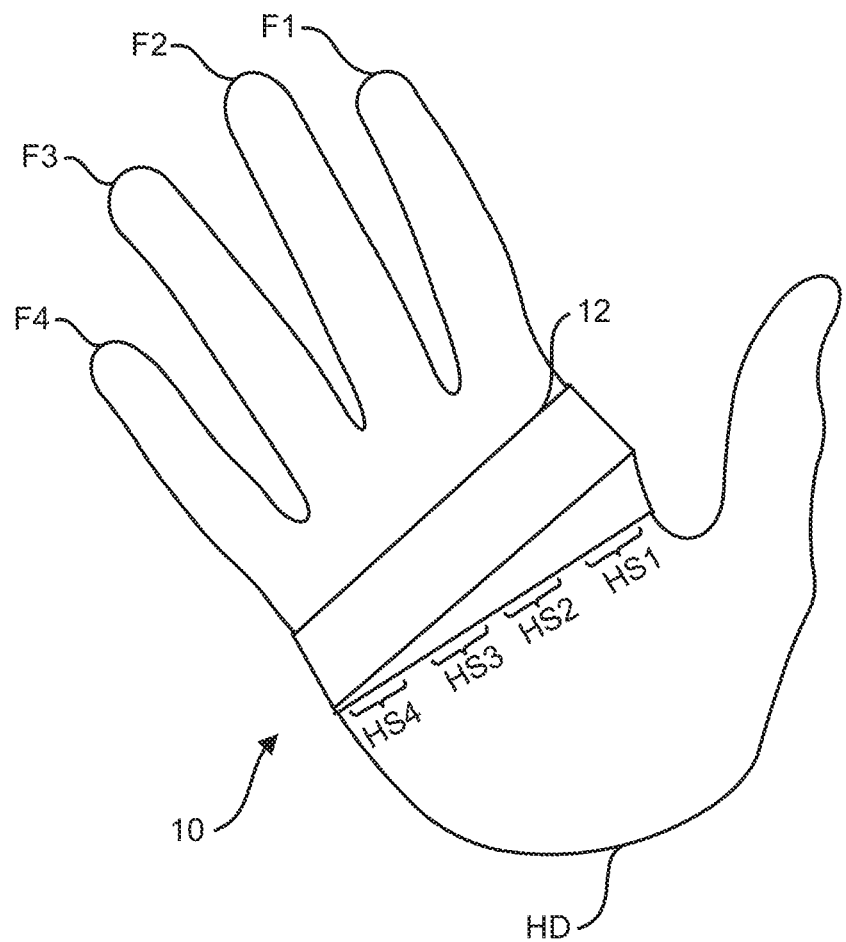
FIG. 3 is a schematic illustration of the handgrip of FIG. 2 secured to the hand.

Referring to FIGS. 2 and 3, one embodiment of a handgrip for positioning the fingers F1-F4 of the hand HD in a desired configuration when grasping the handle HL is generally indicated at reference number 10. The handgrip 10 includes a spacer 12 and a strap 14 for securing the spacer to the hand HD. The spacer 12 is configured to be positioned between the hand HD and the handle HL and thereby elevate certain portions of the hand on the handle. The spacer 12 has a top surface (facing upward in FIG. 2) for engaging the hand HD, a bottom surface (facing downward in FIG. 2) for engaging the handle HL, and a thickness extending between the top and bottom surfaces. (It will be understood that terms of direction such as top, bottom, right, left, etc., refer to the orientation of the features as shown in the drawings and that the orientations of such features will vary in use.) The spacer 12 also has a first end and a second end spaced apart along a length L of spacer. In certain embodiments, the spacer 12 is comprised of a rubber or a plastic, such as polybutadiene, polychloroprene (Neoprene), natural rubber, silicone, high density polyethylene, and PVC. The strap 14 is secured to the spacer 12 adjacent the first and second ends thereof and circumscribes the back of the hand HD in use.

Figure 2A:
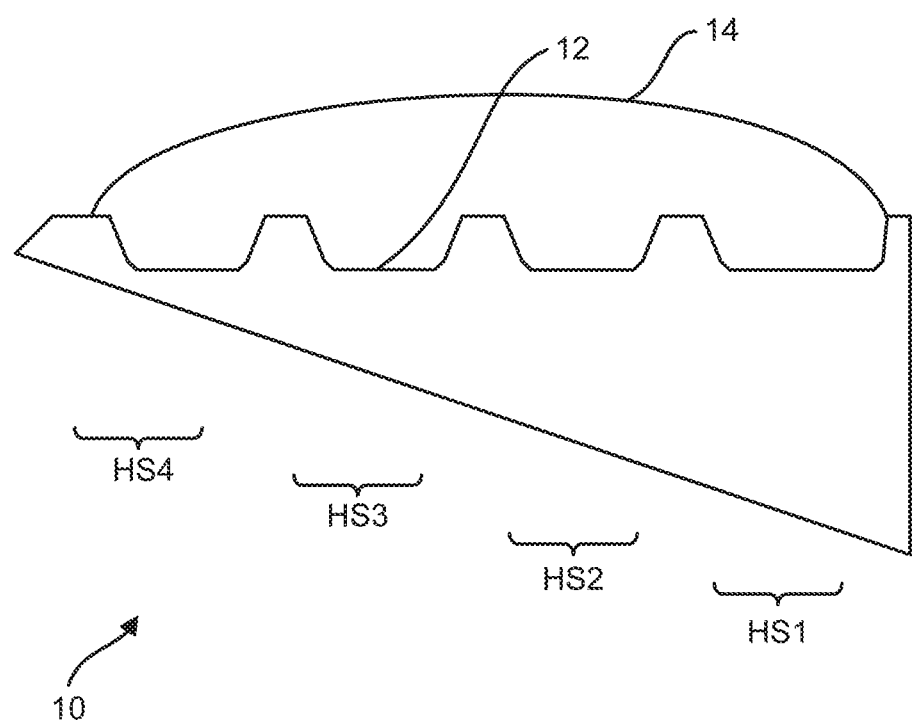
FIG. 2A is a schematic illustration of another embodiment of a handgrip.

In the illustrated embodiment, the length L of the spacer 12 includes a first hand-engaging segment HS1, a second hand-engaging segment HS2, a third hand-engaging segment HS3, and a fourth hand-engaging segment HS4. Other spacers can include other numbers of hand engaging segments in other embodiments. When the strap 14 secures the illustrated spacer 12 to the hand HD such that the top surface engages the palm side of the hand along the metacarpophalangeal joint, the first hand-engaging segment HS1 is aligned with the index finger F1, the second hand-engaging segment HS2 is aligned with the middle finger F2, the third hand-engaging segment HS3 is aligned with the ring finger F3, and the fourth hand-engaging segment HS4 is aligned with the pinky finger F4. Rather than being aligned with the fingers along the metacarpophalangeal joint of the hand HD, the hand-engaging segments of a spacer could be aligned with the fingers along other portions of the hand, such as the proximal phalanges, the middle phalanges, distal phalanges, metacarpal bones, carpal bones, etc. As explained below, a segment of a spacer is "aligned with a finger" when the segment of the spacer supports the finger at a desired position with respect to the handle HL. When the spacer 12 is configured for engagement with the phalanges of the fingers F1-F4, the top surface can be contoured along each hand-engaging segment HS1-HS4 (e.g., finger-engaging segment or phalange-engaging segment) as shown in FIG. 2A. To further retain the top surface of the spacer 12 in its desired position on the hand HD, an adhesive (e.g., a TPU, a resin, etc.) may be disposed on the top surface and/or the hand engaging surface of the strap 14.

Figure 4:
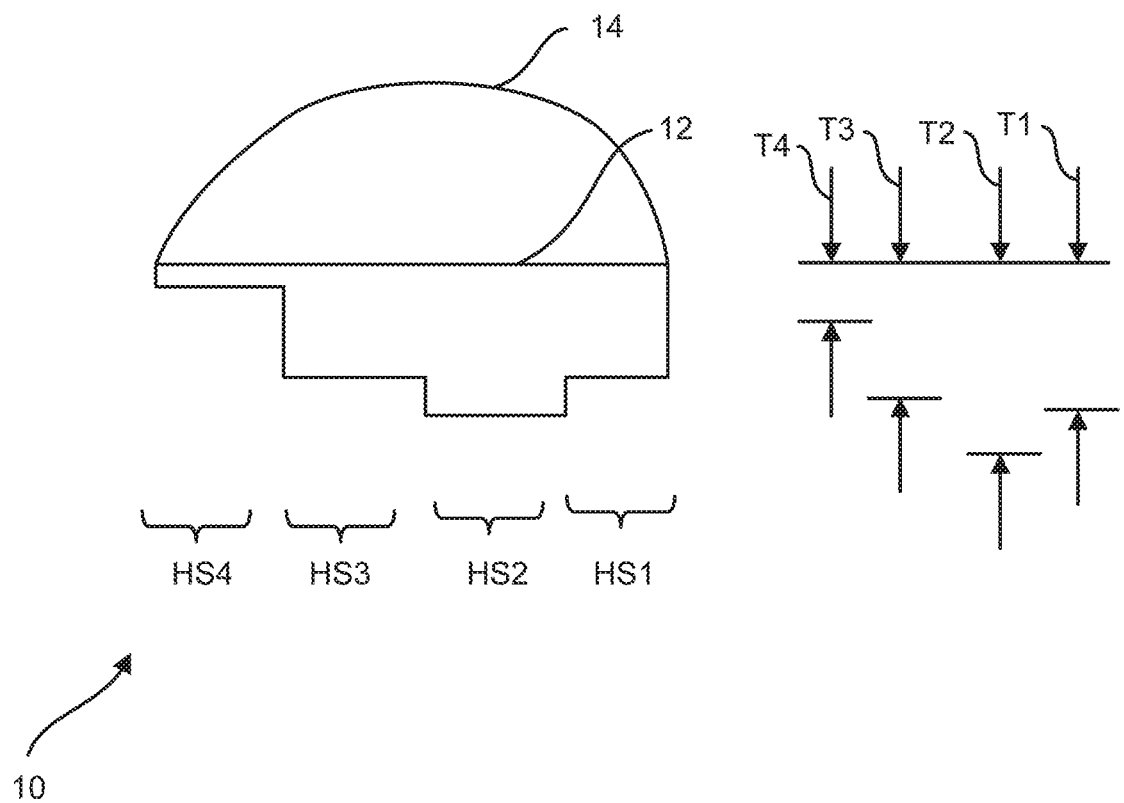
FIG. 4 is a schematic illustration of another handgrip for supporting the hand on the handle.
Figure 5:
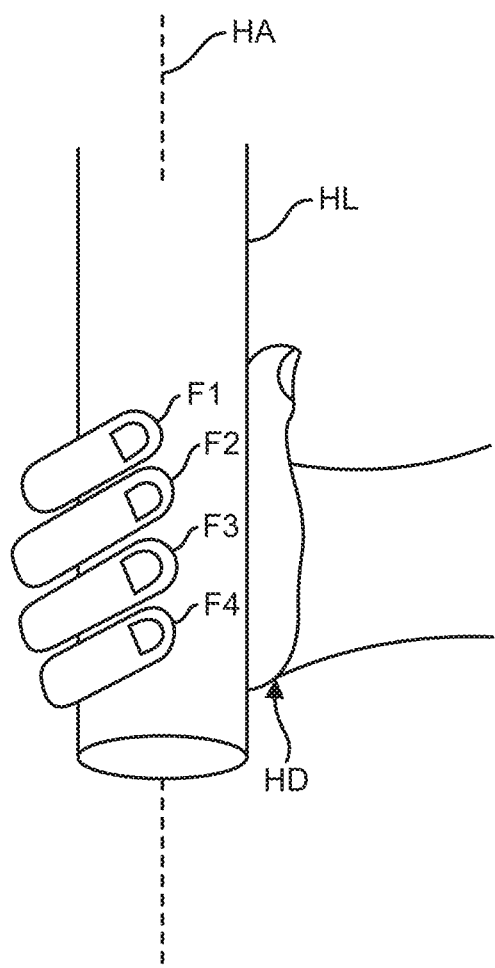
FIG. 5 is a schematic illustration of the hand gripping the handle using the handgrip of FIG. 4.
Figure 6:
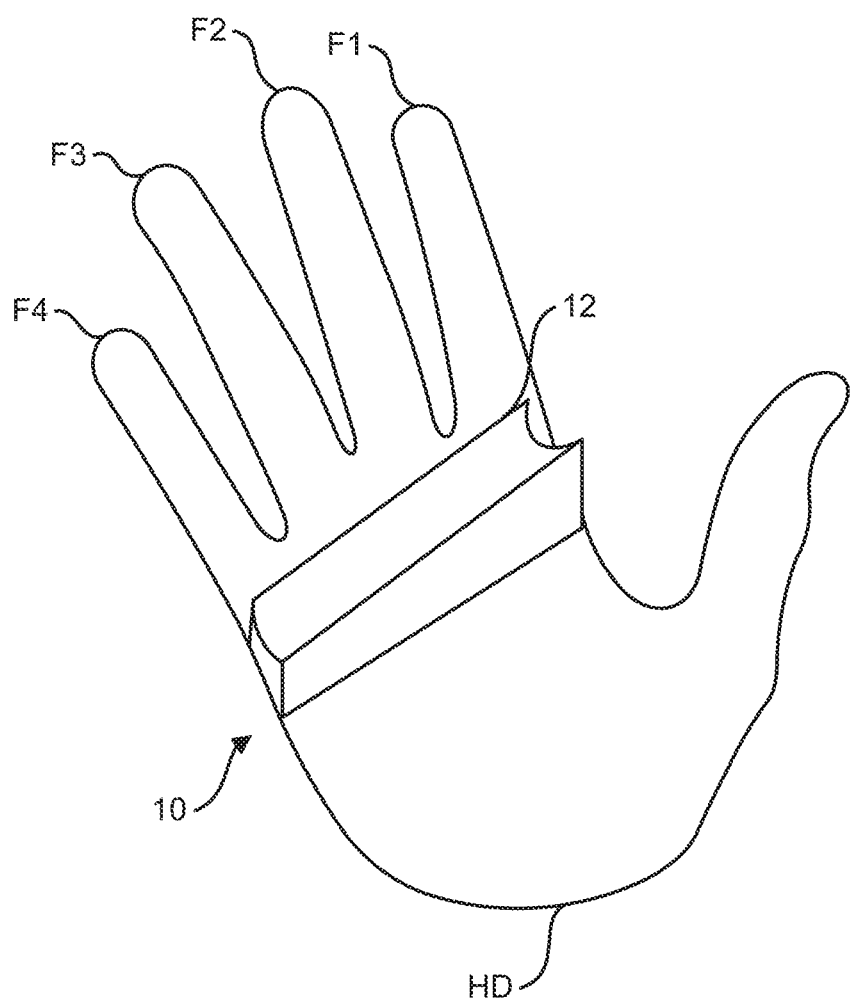
FIG. 6 is a schematic illustration of another embodiment of a handgrip secured to the hand.

Referring again to FIG. 2, the thickness of the spacer 12 varies among at least some of the hand-engaging segments HS1-HS4. In the illustrated embodiment, the spacer 12 has a wedge shape along its length L, with the thickness tapering from the first end to the second end of the spacer. Thus, the thickness of the spacer 12 is largest at the first hand-engaging segment HS1, the second hand-engaging segment HS2 has a greater thickness than the third hand-engaging segment HS3, and the thickness is smallest at the fourth hand-engaging segment HS4. In other embodiments, the thicknesses of the hand-engaging segments can vary in other ways. As shown in FIG. 4, in one embodiment, thicknesses T1-T4 of the hand engaging segments HS1-HS4 vary in accordance with the nominal radii of curvature of the fingers F1-F4 with which they are operatively aligned when the strap 14 operatively secures the spacer 12 to the hand HD. Thus, in FIG. 4, the fourth hand-engaging segment HS4 for alignment with the pinky F4 has the smallest thickness T4, while the second hand-engaging segment HS2 for alignment with the middle finger F2 has the largest thickness T2. Referring to FIG. 5, when the handgrip 10 is used to position the hand HD while grasping the handle HL (the handgrip 10 is concealed by the handle HL in FIG. 5), the tips of the fingers F1-F4 are aligned along the handle axis HA. Aligning the tips of the fingers F1-F4 along the handle axis HA or another desired grip line is thought to equalize the pressure exerted among the fingers in use. To further enhance ergonomics when gripping the handle HL using the handgrip 10, the bottom surface of the spacer 12 can be contoured (e.g., define a groove or other recess) to conform to the perimeter of the handle as shown in FIG. 6. In one embodiment, a spacer 12 is custom-molded to conform to the hand HD of the user.

Figure 7:
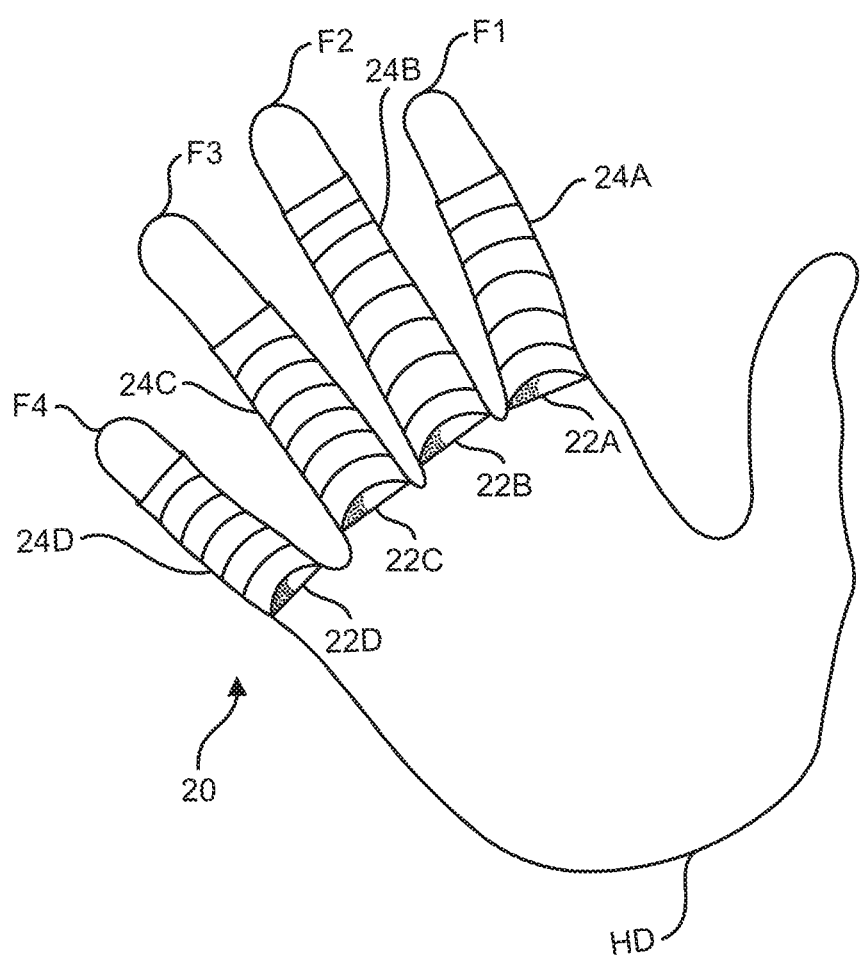
FIG. 7 is a schematic illustration of a kit for supporting fingers of the hand when grasping the handle.

Referring to FIG. 7, a kit for positioning the fingers F1-F4 in a desired configuration when grasping the handle HL is shown installed on the hand HD and generally indicated at reference number 20. In the illustrated embodiment, the kit 20 comprises a spacer comprising individual spacers 22A-22D for each finger F1-F4, and a strap or sleeve 24A-24D for each of the fingers F1-F4. Each spacer 22A-22D is configured for being received between the respective finger F1-F4 and the handle HL. More specifically, each spacer 22A, 22D has a top surface for engaging the respective finger F1-F4, an opposite bottom surface for opposing the handle HL, and a thickness extending between the top and bottom surfaces. Each strap 24A-24D secures the respective spacer 22A-22D to the respective finger (e.g., along the proximal phalange) so that the top surface engages the finger. In the illustrated embodiment, the straps 24A-24D comprise fabric straps that are wrapped around the finger several times. Other types of straps can also be used in other embodiments. In the illustrated embodiment, the thicknesses of the spacers 22A-22D vary in accordance with the radii of curvature of the respective fingers. Thus, like the spacer 12 of the handgrip 10 of FIGS. 4 and 5, the spacers 22A-22D can be configured to align tips of the fingers F1-F4 along the handle axis HA when the hand HD grasps the handle HL. In one or more embodiments, the thickness of each of the spacers 22A-22D tapers distally along the respective finger F1-F4. In some embodiments, the spacers 22A-22D extend substantially the entire length of the fingers F1-F4. In certain embodiments, the distal ends of the spacers 22A-22D are spaced apart proximally from the distal phalanges of the fingers F1-F4. It is understood that kits 20 may be produced in multiple sizes for users having hands HD of different sizes. In addition, the spacers 22A, 22B can be custom-formed to fit the fingers F1-F4 of the user. In addition, the thicknesses of the spacers 22A-22B along their lengths can vary depending on the type of handle HL with which the kit 20 is intended to be used. Grooves, indentations, contours, etc., may be formed in the spacers 22A-22B to suit the cross-sectional shapes of different types of handles HL.

Figure 8:
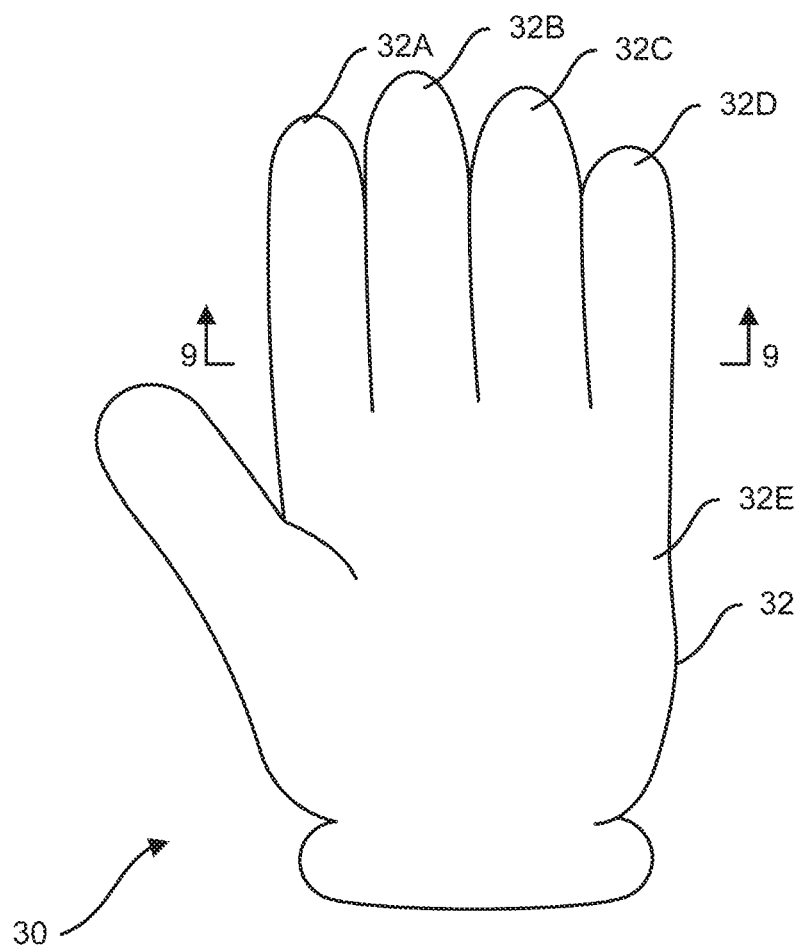
FIG. 8 is a schematic illustration of a glove for supporting the hand when grasping the handle.
Figure 9:
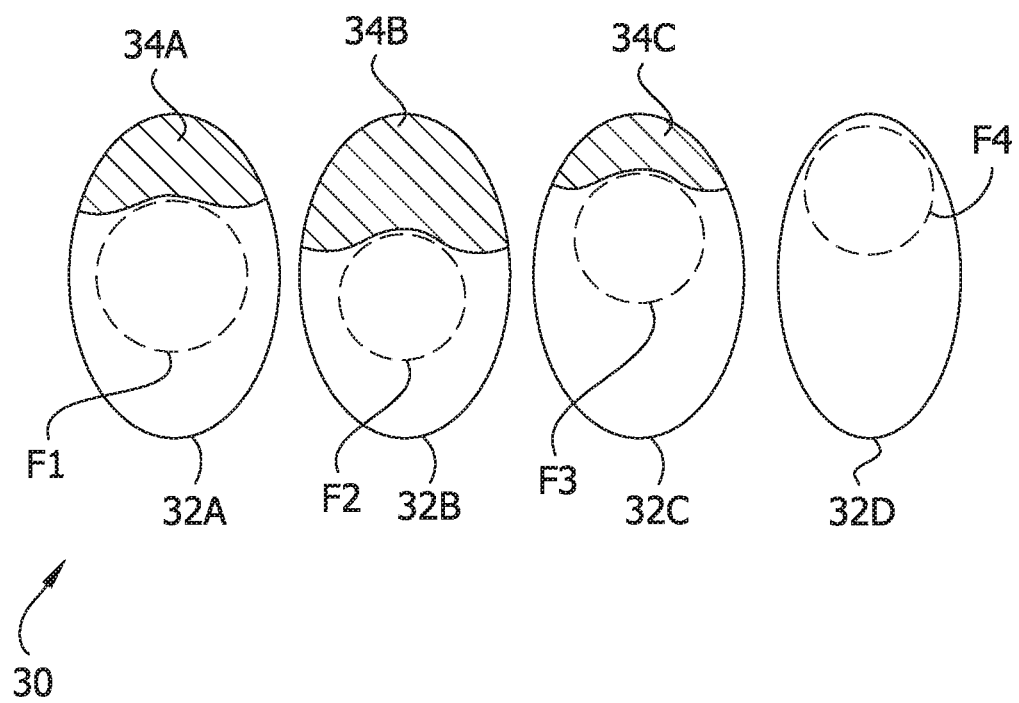
FIG. 9 is a schematic cross-sectional illustration taken in the plane of line 9-9 of FIG. 8.

Referring to FIGS. 8 and 9, a glove for positioning the fingers F1-F4 in a desired configuration when grasping the handle HL is generally indicated at reference number 30. The glove 30 comprises a shell portion 32 including a plurality of finger receptacles 32A-32D for receiving the respective ones of the fingers F1-F4. The finger receptacles 32A-32D extend from a palm enclosure 32E for receiving the palm portion of the hand HD. As shown in FIG. 9, a spacer 34A-34C is attached to each of the finger receptacles 32A-32C for being received between the respective finger F1-F3 and the handle HL when the hand HD grasps the handle while wearing the glove. The spacers 34A-34C have interior surfaces for opposing the fingers F1-F3, exterior surfaces for opposing the handle HL, and varying thicknesses extending between the top surfaces and the bottom surfaces. In the illustrated embodiment, the spacers 34A-34C are secured in the interiors of the receptacles 32A-32C, but the spacers could also be secured to the exterior surfaces of the receptacles in other embodiments. In the illustrated embodiment, no spacer is provided for the pinky receptacle 32D so that the pinky is not elevated with respect to the perimeter of the handle HL when the hand HD grasps the handle. As in the kit 20 of FIG. 7, the spacers 34A-34C are sized and arranged to align the tips of the fingers F1-F4 along the handle axis HA when the hand HD grasps the handle HL.

Figure 10:
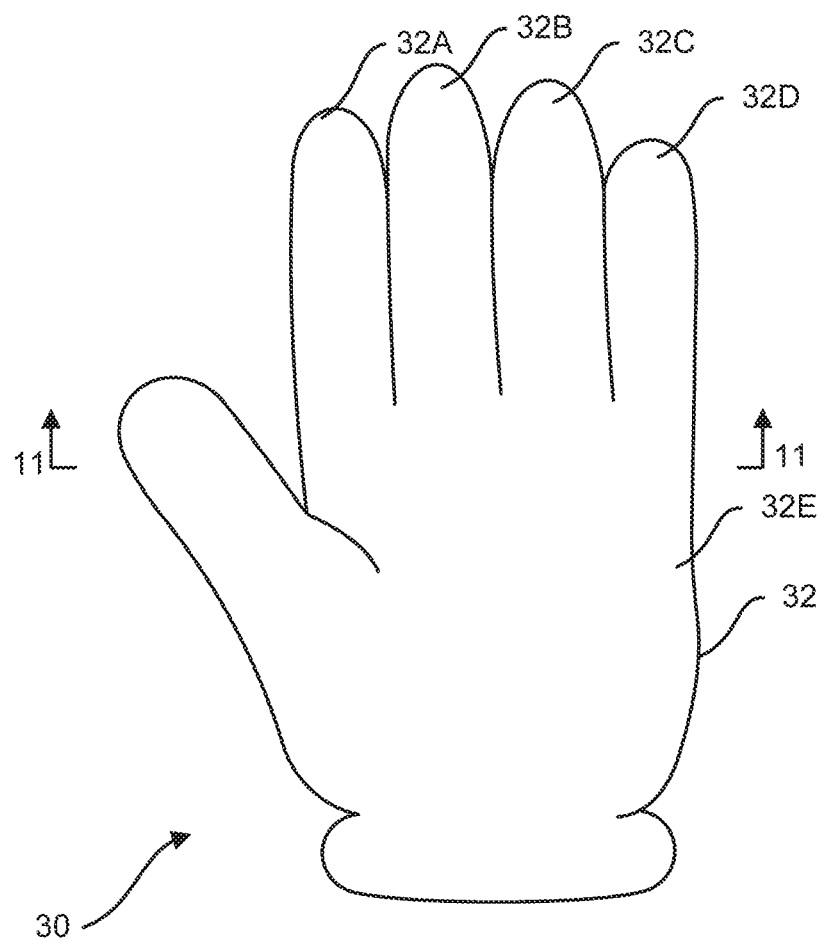
FIG. 10 is a schematic illustration of another embodiment of a glove.
Figure 11:
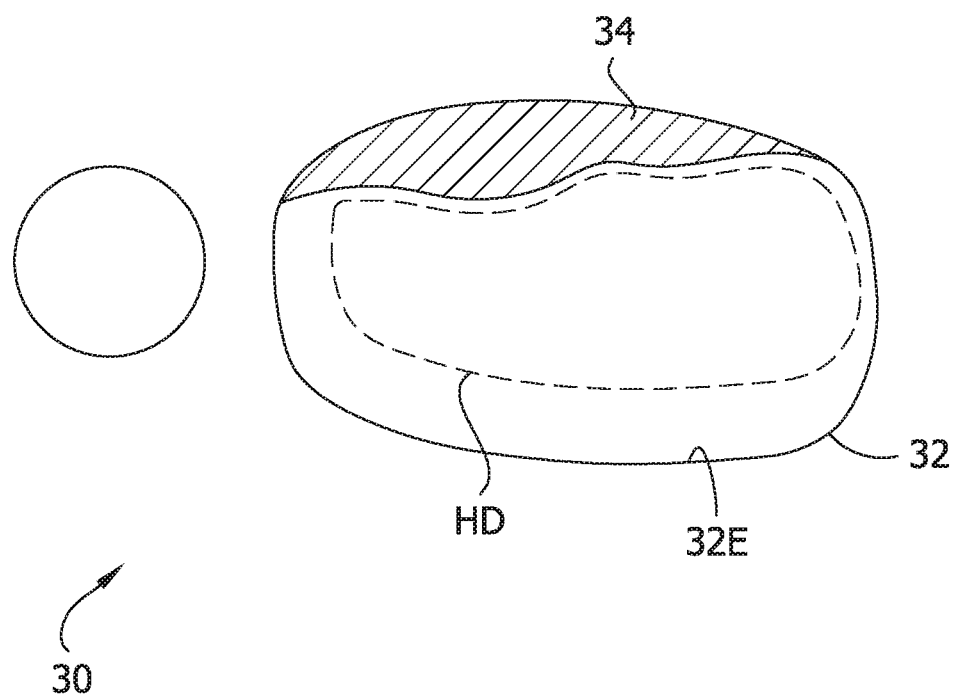
FIG. 11 is a schematic cross-sectional illustration taken in the plane of line 11-11 of FIG. 10.

Instead of securing the spacers 34A-34C on the finger receptacles 32A-32C, other embodiments can include a spacer mounted at another location of the glove 30. For example, referring to FIGS. 10 and 11, in another embodiment a glove 30 includes a spacer 34 comprising a single, integrally formed one-piece body secured to the palm enclosure 32E for being operatively aligned with the metacarpophalangeal joint of the hand HD as described above in reference to the spacer 12 of FIGS. 2 and 3.

In each embodiment of the glove 30, the spacers 34, 34A-34C could be modular. That is, each spacer 34, 34A-34C could comprise a plurality of stackable spacer elements that can be selectively added or removed to adjust the thickness of the spacer. In one specific embodiment, modular spacers 34A-34C are added to the finger receptacles 32A-32C to position a weak one of the fingers F1-F4 out of line with the other fingers in a position where less force is imparted on the weak finger than the other fingers when the hand HD maneuvers the handle HL. In other embodiments, the spacers 34, 34A-34C each comprises an inflatable bladder that is selectively inflatable/deflatable using a fitting accessible from the exterior of the glove 30 to adjust the thickness of the spacer.

The gloves 30 (or another type of glove, such as the glove 510 discussed below) can, in some embodiments, include one or more sensors configured to provide data, such as biometric data about the wearer, grip force data representing a force with which the wearer grips an item, environmental data representative of one or more parameters of an environment in which the glove is worn or used, etc. Thus, in one or more embodiments, a glove comprises a biometric sensor, a grip force sensor, an environmental sensor, etc. The data can be used, for example, for biometric monitoring, activity tracking, analyzing a subject's biodynamic response to hand movements, monitoring exposure to certain hazardous or therapeutic substances, monitoring environmental conditions in which the glove is present, providing a control input to a robotic device such as a robotic exoskeleton or biomimetic robot, etc. The data can be transmitted wirelessly or by a wired connection to a receiver such as a controller, a patient monitoring system (see related patents, referenced infra), a server running a tracking application related to the data, etc. The receiver can maintain a record of the data, use the data to provide a diagnosis or prescribe treatment or therapy, control a controllable feature of the glove or a separate device, etc.

Figure 12:
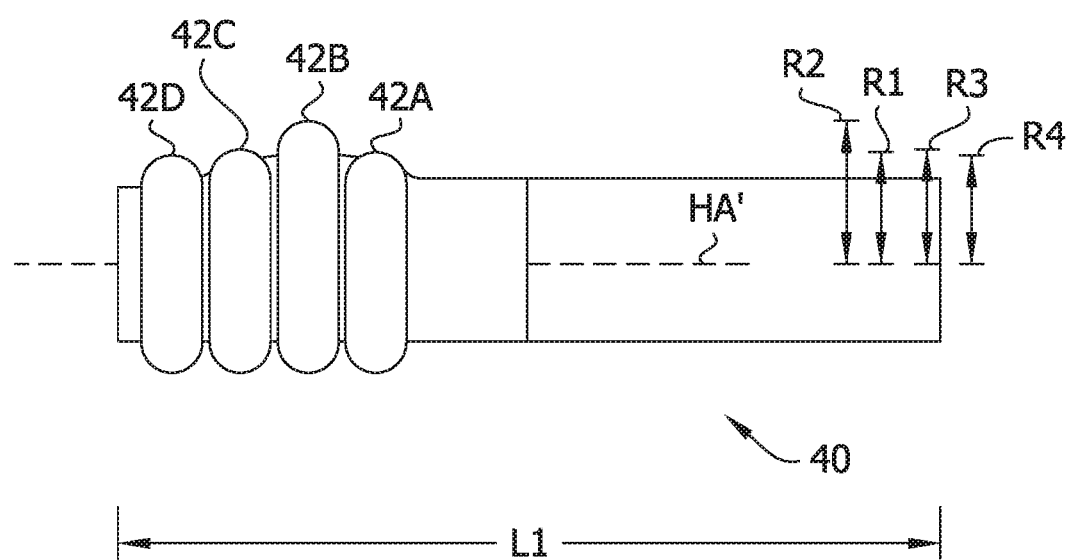
FIG. 12 is a schematic illustration of a handle for supporting the hand so that the tips of the fingers are aligned.
Figure 13:
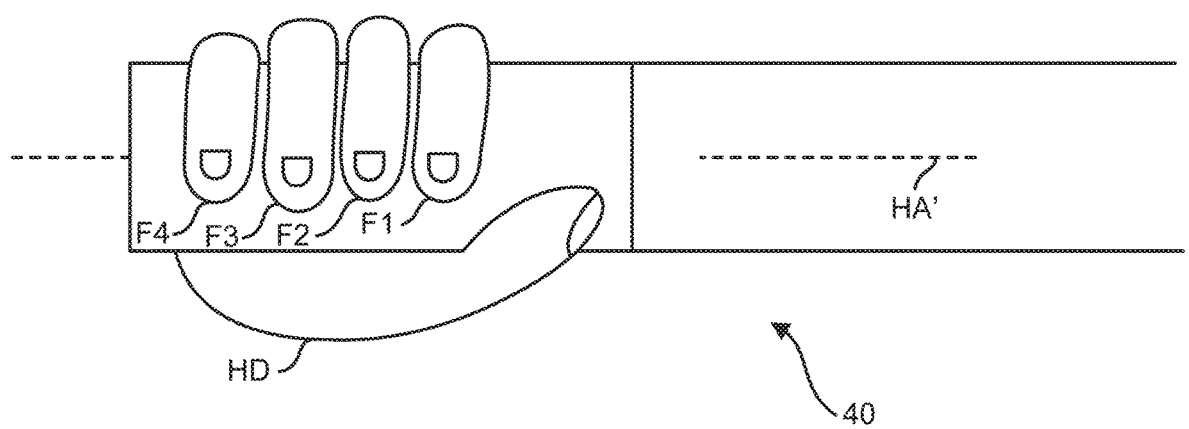
FIG. 13 is a schematic illustration of the hand grasping the handle of FIG. 12.

Referring to FIG. 12, one embodiment of a handle for aligning the tips of a user's fingers F1-F4 is generally indicated at reference number 40. The handle 40 has a first end, a second end, and a length L1 extending along an axis HA' from the first end to the second end. The illustrated handle 40 includes a first hand-engaging spacer 42A extending along a first segment of the length L1 for supporting a portion of the hand aligned with the index finger F1 when the hand grasps the handle, a second hand-engaging spacer 42B extending along a second segment of the length L1 for supporting a portion of the hand aligned with the middle finger F2 when the hand grasps the handle, a third hand-engaging spacer 42C extending along a third segment of the length L1 for supporting a portion of the hand aligned with the ring finger F3 when the hand grasps the handle, and a fourth hand-engaging spacer 42A extending along a fourth segment of the length L1 for supporting a portion of the hand aligned with the pinky finger F1 when the hand grasps the handle. As shown in FIG. 13, the supports 42A-42D are shaped and arranged to align the tips of the fingers F1-F4 along a grip axis, which in the illustrated embodiment is coincident with the handle axis HA' when the hand HD grasps the handle 40 and each finger curves around and engages the respective support. More specifically, each support 42A-42D has a maximum radius R1-R4, and the maximum radii of the supports 42A-42D vary in accordance with the radius of curvature of the respective fingers F1-F4. Various portions of the hand HD may engage the section of the support 42A-42D that defines the maximum radius R1-R4 as explained above in reference to the spacers 12 of FIGS. 1-6. Although the illustrated embodiment is configured to align the tips of the four fingers F1-F4 along the handle axis HA', other embodiments can be configured to align other numbers of fingers along other axes.

Figure 14:
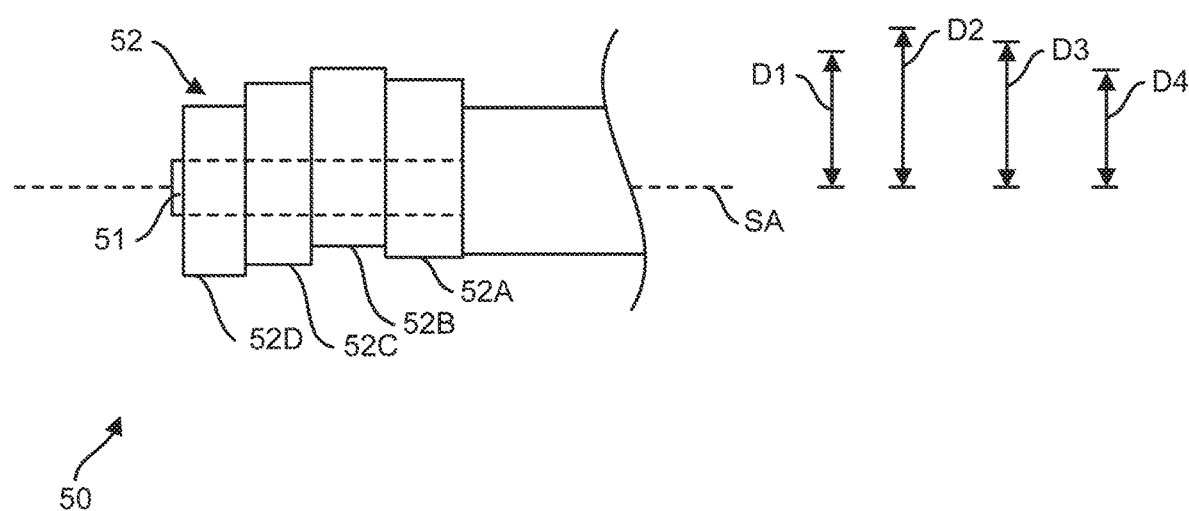
FIG. 14 is a schematic illustration of another handle.
Figure 15:
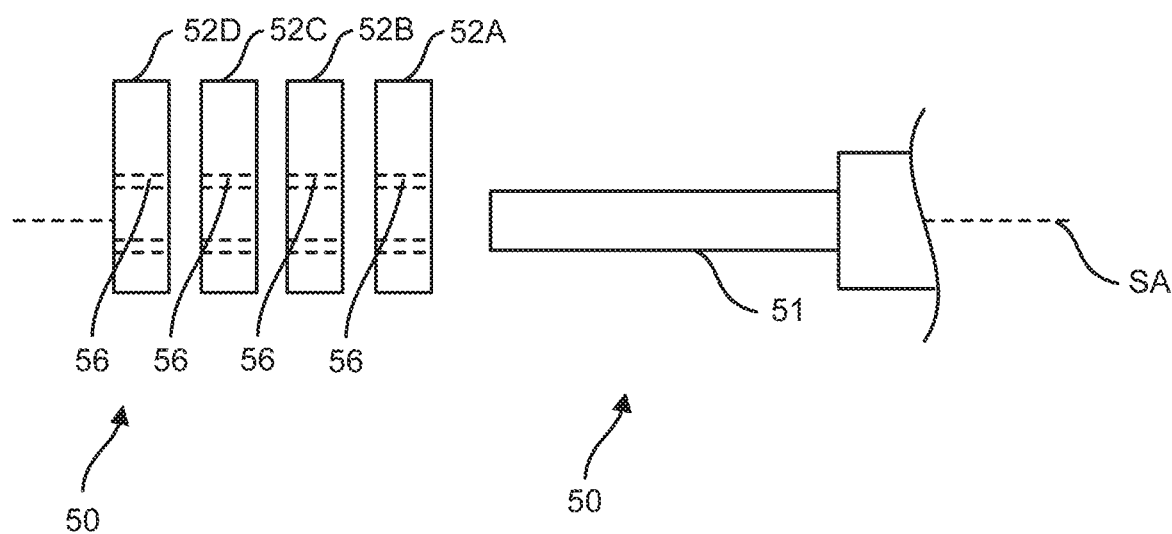
FIG. 15 is a schematic exploded illustration of the handle of FIG. 14.

Referring to FIGS. 14-15, another embodiment of a handle for positioning a user's fingers F1-F4 in a desired configuration is generally indicated at reference number 50. The handle 50 comprises a shaft 51 having an axis SA and a handgrip 52 mounted on the shaft. The illustrated handgrip 52 comprises four hand-engaging members 52A-52D mounted on the shaft 51 at spaced apart locations along the axis SA for being aligned along the shaft axis with respective fingers F1-F4 when the hand HD grips the handle 50. Each hand-engaging member 52A-52D has a perimeter surface that extends circumferentially about the shaft axis SA. Each perimeter surface has a radial position that varies as the surface extends circumferentially around the axis. The hand-engaging members 52A-52D are selectively rotatable about the shaft axis SA with respect to the shaft to configure the handgrip 52 to have the desired shape and arrangement. For example, in FIG. 14 the hand-engaging members 52A-52D are rotated about the axis SA so that the top portions of the fingers are spaced apart from the shaft axis by radial distances D1-D4 that correspond with the radii of curvature of the fingers F1-F4 with which they are aligned when the hand HD grips the handle 50 in use. As shown in FIG. 15, in one or more embodiments, the handgrip 52 includes one or more locking mechanisms 56 for selectively locking each of the hand-engaging members 52A-52B in the desired circumferential position with respect to the shaft 51. Suitable locking mechanisms may include a set screw, a ratchet mechanism, a friction clamp, etc.

Figure 36:
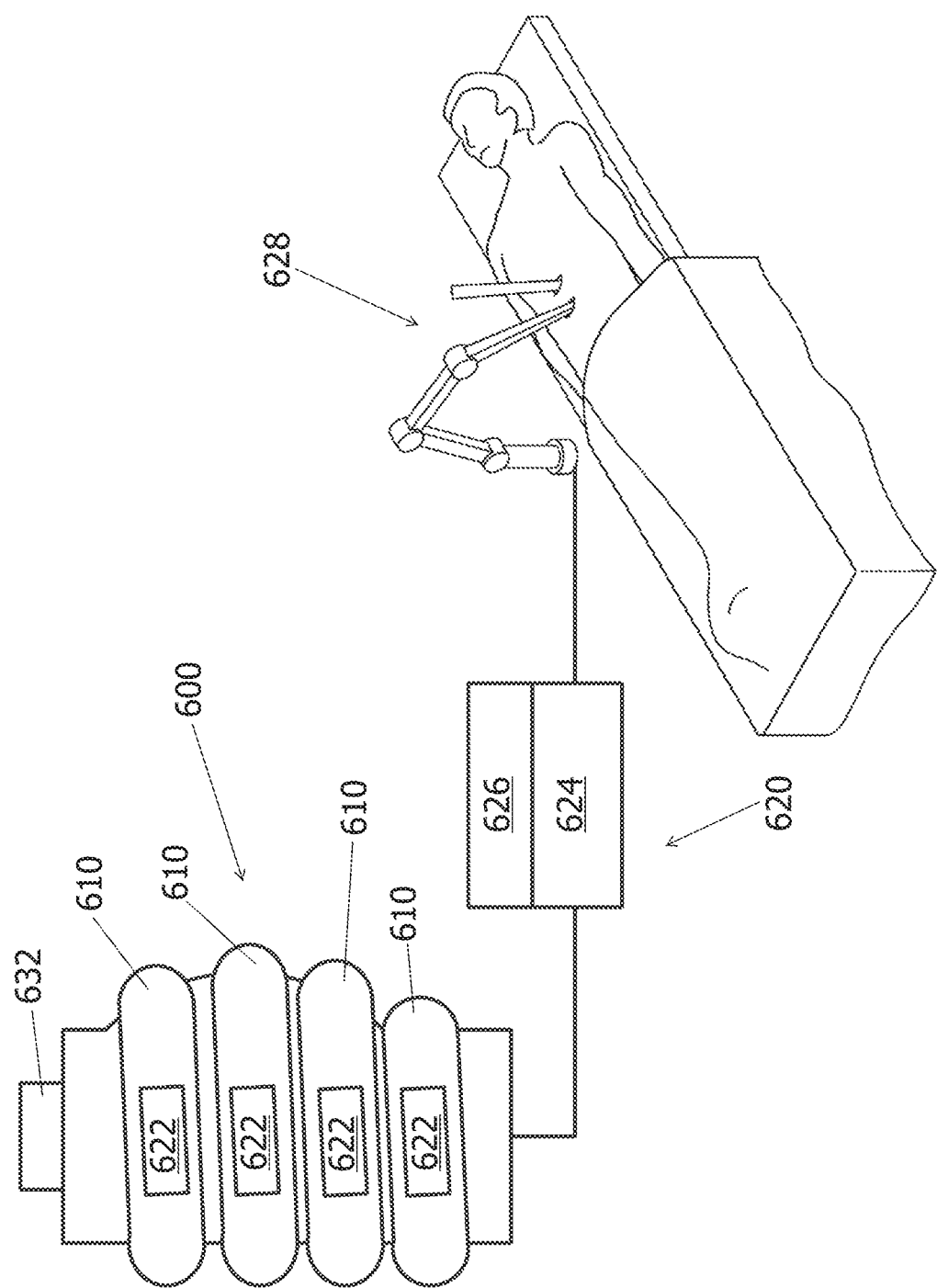
FIG. 36 is a perspective of a surgical robot conducting a surgery on a patient, schematically illustrating a handle and a haptic feedback system of the surgical robot.

Referring to FIG. 36, a handle 600 for a surgical instrument comprises hand-engaging portions 610, which can have any of the features of the spacers or hand-engaging portions described elsewhere in this disclosure. As explained above, the handle 600 and the hand-engaging portions 610 are configured to position a surgeon's fingers in an ergonomic position while grasping the handle of the surgical instrument.

In the illustrated embodiment, the handle 610 further includes a haptic feedback system 620. For example, vibrators 622 (broadly, haptic feedback outputs) can be incorporated in the handle to impart vibration (broadly, haptic feedback) to the surgeon's hand in use. In one embodiment, the vibrators are positioned in or on the hand engaging portions 610 of the handle 600. The haptic feedback system 620 can include a controller 624 for controlling the vibrator based on a preprogrammed control routine that is stored in a memory 626. The haptic feedback control routine can be responsive to certain control inputs related to the surgical procedure.

In one exemplary embodiment, the handle 610 comprises a control handle for controlling a surgical robot 628. It is understood that the handle could be used with other surgical instruments in other embodiments. Various surgical robots 628 are known. Exemplary surgical robots are described in U.S. Patent Application Publication No. 2017/0281254, which is hereby incorporated by reference in its entirety. The handle 600 includes one or more control inputs 632 for performing a surgical task using the robot 628. For example, the control input 632 can be responsive to movement of one or more of a surgeon's fingers, thumb, and palm while grasping the handle. In one or more embodiments, the robot 628 comprises an arm configured to selectively grasp tissue and/or a surgical implement. In certain embodiments, the arm and the control input 632 are configured for biomimetic surgical control (e.g., the arm can include a hand mechanism with limbs that grasp in a manner that mimics the grasping motion of a portion or all of a surgeon's hand while holding the handle 600). The haptic feedback system 620 incorporated in the handle can be responsive to signals provided by one or more sensors on the robot 628. For example, the haptic feedback system 620 can be configured to provide haptic feedback that varies in intensity and location to provide an indication of forces imparted on the robot by tissue or surgical instruments during a surgical procedure. The haptic feedback system 620 can also be used to alert the surgeon when the surgeon manipulates the handle in a manner that robot 628 does not recognize or is otherwise not permitted under the circumstances. The haptic feedback system 620 can also be used as a real-time corrective when training the surgeon to use the surgical robot 628.

Any of the handles described above (or another type of handle) can, in some embodiments, include one or more sensors configured to generate a signal including sensed data, such as biometric data about the user, data representing forces imparted on the handle by the user or another source, environmental data representative of one or more parameters of an environment in which the handle is used, etc. Thus, in one or more embodiments, a handle comprises a biometric sensor, a grip force sensor, an environmental sensor, a movement sensor, etc. The data can be used, for example, for biometric monitoring, activity tracking, analyzing a subject's biodynamic response to using the handle, analyzing the movement patterns of the handle, the providing a control input to a robotic device such as a robotic exoskeleton, a robotic prosthetic, a biomimetic robot, etc. The data can be transmitted wirelessly or by a wired connection to a receiver such as a controller, a patient monitoring system, a server running a tracking application related to the data, etc. The receiver can maintain a record of the data, use the data to provide a diagnosis or prescribe treatment or therapy, control a controllable feature of the handle or a separate device, etc.

Figure 16A:
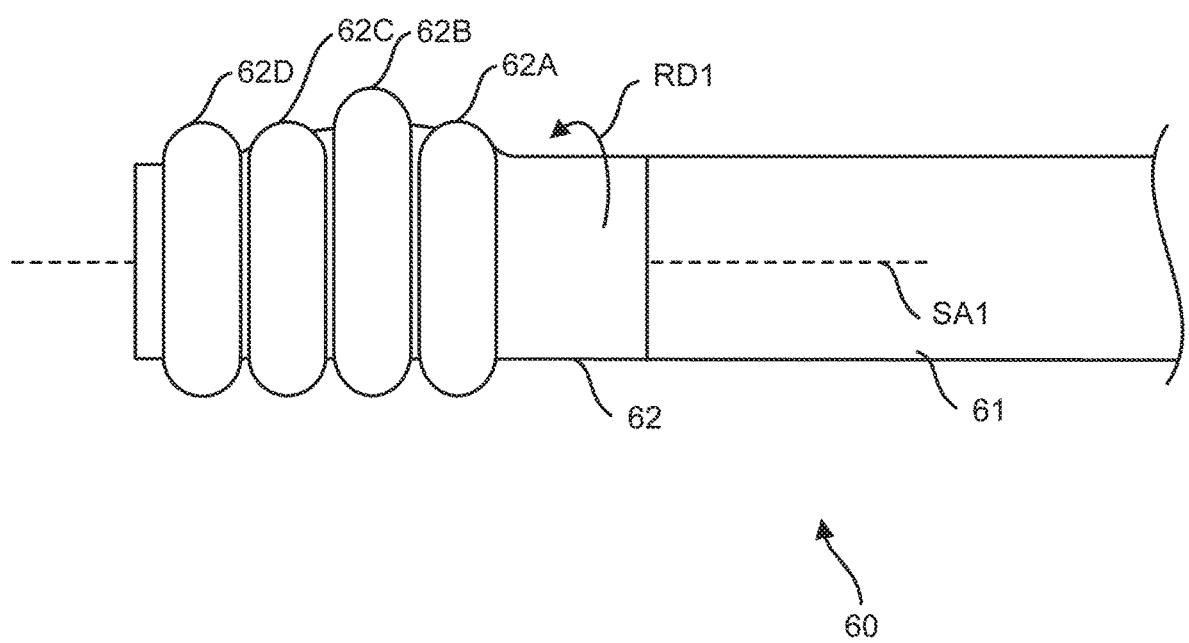
FIG. 16A is a schematic illustration of another embodiment of a handle with a handgrip thereof shown in a first position.
Figure 16B:
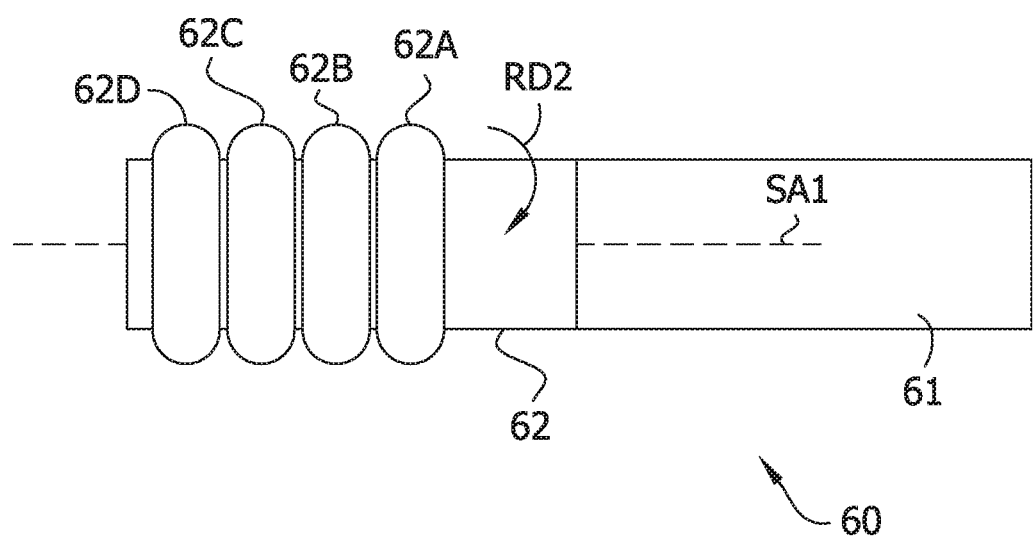
FIG. 16B is a schematic illustration of the handle of FIG. 16A illustrating the handgrip in a second position.

Certain sports implements require different grip orientations during play. For example, tennis is played at a minimum using a forehand grip and a different backhand grip. For sports such as tennis, it may be necessary for a player to rapidly change between grip orientations. However, to limit undue stress on a user's hand HD, it may be beneficial to accommodate the varying radii of curvature of the fingers F1-F4 in the multiple grip orientations. Referring to FIGS. 16A and 16B, one embodiment of a handle for positioning a user's fingers F1-F4 in a configuration that accounts for the variance in radius of curvature while permitting selectively adjusting the grip orientation of the hand is generally indicated at reference number 60. The handle 60 includes a shaft 61 having an axis SA1 and a handgrip 62 mounted on the shaft for rotation with respect to the shaft about the shaft axis through a range of motion including a first position (FIG. 16A) and a second position (FIG. 16B). In the illustrated embodiment, the handgrip 62 has the same shape and arrangement as the handgrip portion of the handle 40 shown in FIG. 12. Thus, the handgrip 62 accounts for the variance in the radii of curvature of the fingers F1-F4 using hand-engaging spacers 62A-62D of different radial dimensions. In other embodiments, the handgrip 62 could have other configurations. (For example, in some embodiments, the handgrip 62 is a modularly adjustable handgrip with separately adjustable hand-engaging spacers such as the handgrip 52 shown in FIG. 14.) But suitably, the handgrip 62 includes at least two hand-engaging spacers extending along respective segments of the length of the handgrip to support a portion of the hand HD grasping the handle aligned with at least two of the fingers F1-F4 to align the fingers in a desired configuration when the hand grasps the handle 60.

Figure 16C:
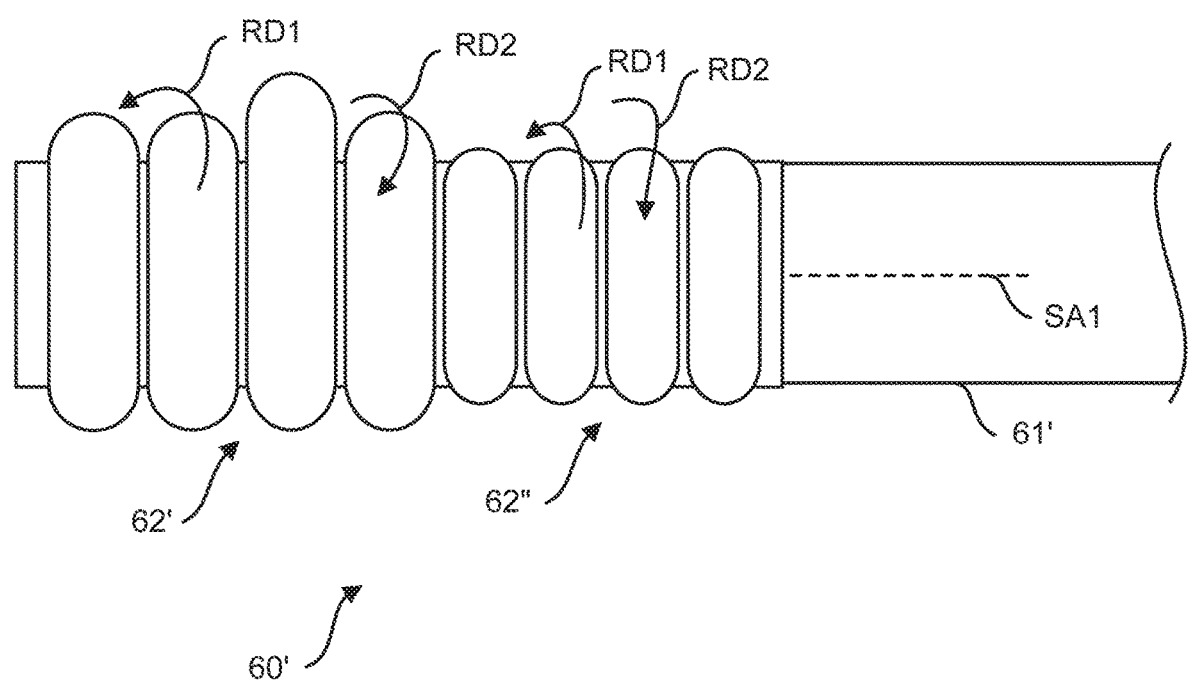
FIG. 16C is a schematic illustration of another embodiment of a handle.

In the illustrated embodiment, the first position (FIG. 16A) in the range of motion of the handgrip 62 corresponds with a one-handed overhand grip of a tennis racket and the second position (FIG. 16B) corresponds with a one-handed backhand grip. The handgrip 62 is rotatable with respect to the shaft 62 from the first position to the second position in a first direction RD1 and from the second position to the first position in a second direction RD2. Suitably, the handle 60 may include stops or detents that indicate when the handgrip 62 is positioned in the first and second positions. It is understood that the handgrip could have more than two positions that are indicated as the handgrip travels through its range of motion. In addition, it is understood that two rotatably mounted handgrips could be used to account for variations in two-handed grip orientations during gameplay. For example, FIG. 16C illustrates one embodiment of hand grip having a first handgrip 62' for a first hand and a second handgrip 62" that are each selectively rotatable about a shaft axis SA1 with respect to a shaft 61' in first and second directions RD1, RD2 for adjusting the grip orientations of first and second hands on the handle 60'.

Referring again to FIG. 16A, in certain embodiments, the hand grip 62 is configured to be rotated an entire revolution about the shaft axis SA1 and includes a plurality of predetermined stop positions at circumferentially spaced positions about the axis. For example, in one embodiment, the handgrip 62 has eight stop positions that are circumferentially spaced apart from one another by about 45°. In other embodiments, a handle 60 can have other numbers of stop positions. At each stop position, the handgrip 62 is configured to click or lock into place. For example, the handgrip 62 can include a ratchet mechanism having a pawl that engages a ratchet tooth at desired circumferentially spaced intervals to lock the handle into position at each stop position. Suitably, the handle 60 includes a release mechanism (e.g., a push button or the like) for disengaging the locking mechanism (e.g., disengaging the pawl from the ratchet tooth) to allow further rotation of the handgrip 62 about the axis SA1 during play. Other types of locking mechanisms and release mechanisms may be used in other embodiments. In addition, instead of having predetermined stop positions, the handgrip 62 can be configured to rotate to any circumferential position about the shaft axis SA1 (e.g., the handgrip can be infinitely adjustable about the axis). Suitably, such a handle 60 includes a selectively actuatable locking mechanism (e.g., a friction clamp or the like) that can be used during game play to lock the handgrip 62 in the desired position and quickly unlock the handgrip to rotate it about the shaft axis SA1.

Figure 17:
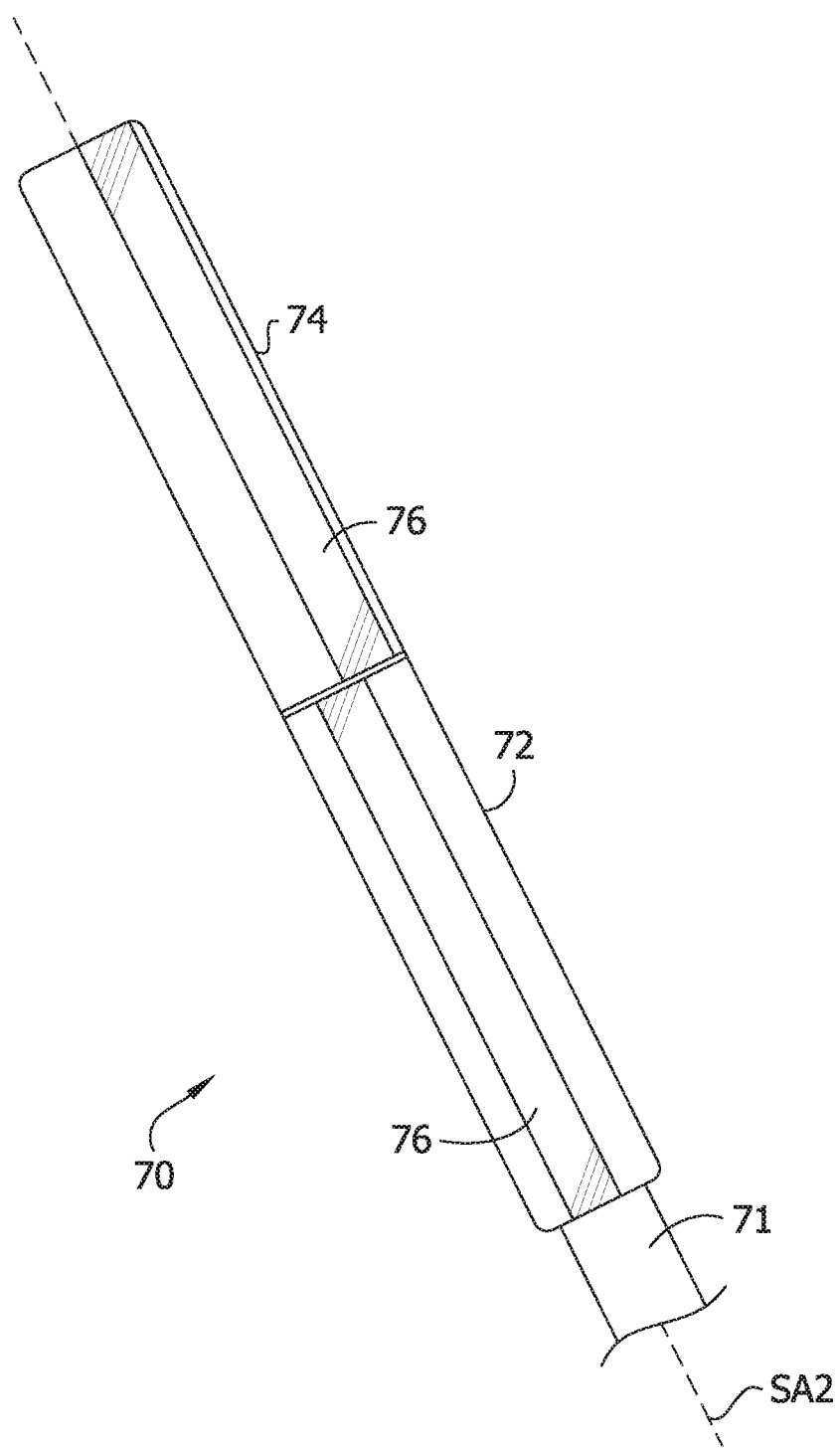
FIG. 17 is a schematic illustration of an adjustable handle of a golf club.

Referring to FIG. 17, an adjustable golf club handle is generally indicated at reference number 70. The handle 70 includes a shaft 71 having an axis SA2. First and second handgrips 72, 74 are mounted on the shaft 71 adjacent the distal end thereof. Each handgrip 72, 74 is configured for being grasped by a respective hand HD (i.e., a left hand or a right hand) of a golfer, and each handgrip includes a perimeter extending circumferentially around the axis SA2. Each handgrip 72, 74 also defines a respective indicator formation 76 that extends along the axis SA2 and provides a tactile indication to the golfer of the circumferential position of the hand HD on the handle 70 when the hand is gripping the handgrip 72, 74. In the illustrated embodiment, the indicator formation comprises a flat side of the respective handgrip 72, 74 (e.g., the cross-sectional shape of the handgrip in a plane orthogonal to the axis SA2 is generally round, except for a flat side that defines the indicator formation), though other indicator formations may also be used in other embodiments. At least one of the first and second handgrips 72, 74 is rotatable with respect to the shaft 71 and the other handgrip about the axis SA2. In the illustrated embodiment, each of the handgrips 72, 74 is rotatable with respect to the shaft 71. The handgrips 72, 74 can be selectively rotated to a desired position and then locked into place (e.g., using a ratchet mechanism, a clamping mechanism, a set screw, etc.). The handgrips 72, 74 can be rotated to adjust the left and right hand grips of the golfer to, for example, account for undesirable aspects of the golfer's swing, correct consistent hooks/slices, etc. Most golfers would be expected instinctively select the orientation of each of their hands HD on the handle 70 based on its respective orientation with respect to the indicator 76. (e.g., by instinctively positioning the hand so that the thumb or palm rests on the flat surface) Thus, by adjusting the circumferential positions of the indicator formations 76 with respect to the axis SA2, the natural orientations of the hands HD of the golfer addressing the handle 70 can be adjusted to correct for faults in the golfer's grip, swing, etc. To further customize the handgrips 72, 74 to a particular golfer's swing, grip, etc., the handgrips may include a plurality of sections along their lengths, each comprising different materials. For example, one section may comprise a deformable material and another section may comprise a more rigid material. Adjusting the material characteristics of the handgrips will naturally adjust the golfer's grip and thereby may be used to improve a golfer's swing.

Biometric analyzers are used to sense and analyze biometric data. Certain biometric analyzers can be mounted on the wrist of a user using a wristband. To provide uninterrupted sensing of biometric data, it is important to maintain the biometric analyzer at an operative position with respect to the wrist for sensing biometric data from the wrist. Typical wristbands are not adapted to the wrist anatomy and thus must be tightened firmly against the wrist to effectively limit movement of a biometric sensor on the wrist when the wrist moves in, for example, flexion, extension, pronation, supination, etc. It is often uncomfortable to tighten a wristband to the necessary degree, so biometric sensors are often loosely secured to the wrist and move with respect to the wrist in use, adversely affecting the quality and quantity of biometric data collected.

Figure 18:
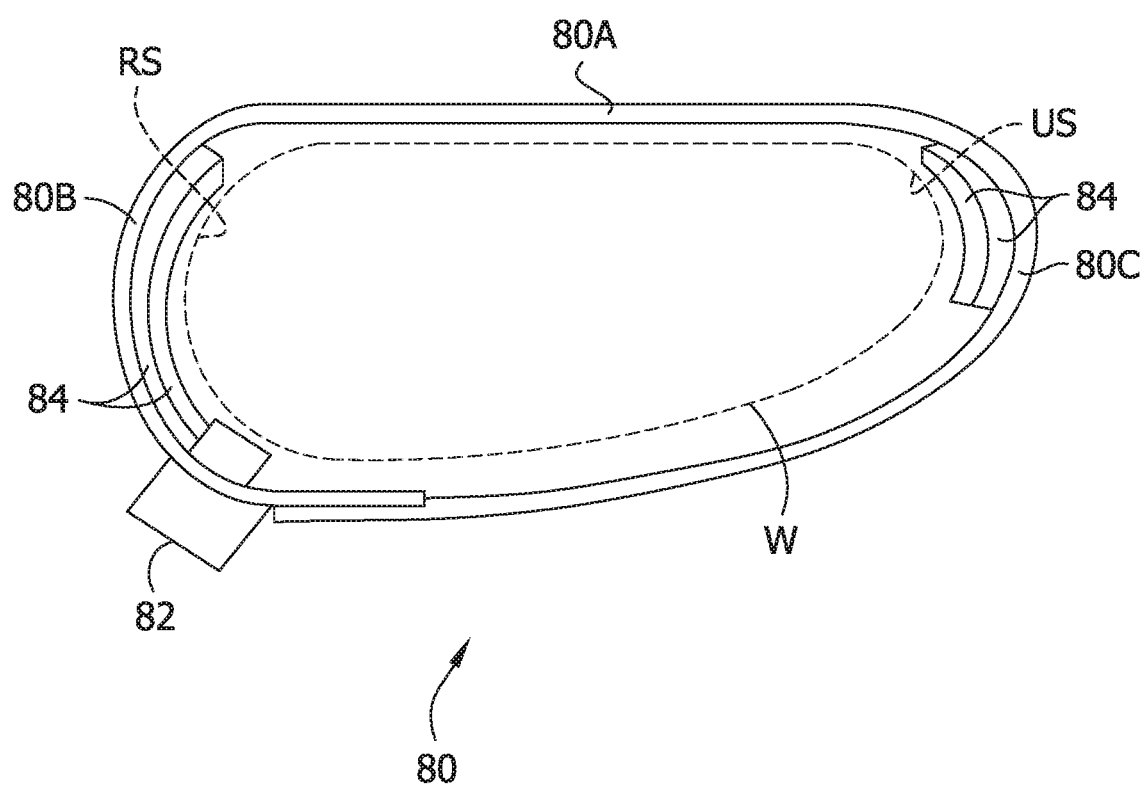
FIG. 18 is a schematic illustration of a wristband supporting a biometric analyzer on a wrist.

Referring to FIG. 18, one embodiment of a wristband that is configured for conforming to the anatomy or a user's wrist W is generally indicated at reference number 80. The wrist W includes a radius side portion RS and an ulna side portion US. The wristband 80 supports a biometric analyzer 82 for being operatively positioned in engagement with the user's wrist W. For example, the illustrated wristband 80 is configured to position the analyzer 82 in circumferential alignment with the radial artery of the wrist W. Other wristbands can be configured to position analyzers at other circumferential positions of the wrist. The wristband 80 has a top segment 80A having a first end and a second end. A radius side segment 80B for conformingly engaging the radius side portion RS of the wrist W extends from the first end of the top segment 80A, and an ulna side segment 80C for conformingly engaging the ulna side portion US of the wrist extends from the second end of the top segment. Suitably, the wristband 80 can be formed of a strap of resiliently conformable material. For example, the radius side segment 80B can be resiliently biased to have a first radius of curvature and the ulna side segment 80C can be resiliently biased to have a second radius of curvature that is smaller than the first radius of curvature. Suitably, the radii of curvature of the radius side segment 80B and the ulna side segment 80C are generally matched to the anatomy of the wrist W.

In the illustrated embodiment, the wristband 80 includes a plurality of modular spacers 84. Each spacer 84 is suitably formed of a compressible material shaped to have about the same width as the band 80, to have a length for extending along the radius side portion 80B or the ulna side portion 80C, and to have a thickness. A selected number of spacers 84 are secured (e.g., using adhesives, fasteners, etc.) to the interior surface of one or both of the radius side segment 80B and the ulna side segment 80C of the wrist band 80 to increase the thickness of the respective portion of the wrist band for conformingly engaging the wrist W. Suitably, the end segments of the radius side segment 80B and the ulna side segment 80C can be clasped together to secure the wristband to the wrist W. The spacers 84 on the radius side segment 80B conformingly engage the radius side portion RS of the wrist W and the spacers 84 on the ulna side segment 70C conformingly engage the ulna side portion US of the wrist to maintain the wristband 80 in the desired circumferential orientation on the wrist, even during flexion, extension, pronation, supination, etc. Instead of using modular spacers 84, the thickness of the side segments 80B, 80C of the band 80 may be adjusted using inflatable bladders mounted at the same positions.

Figure 19:
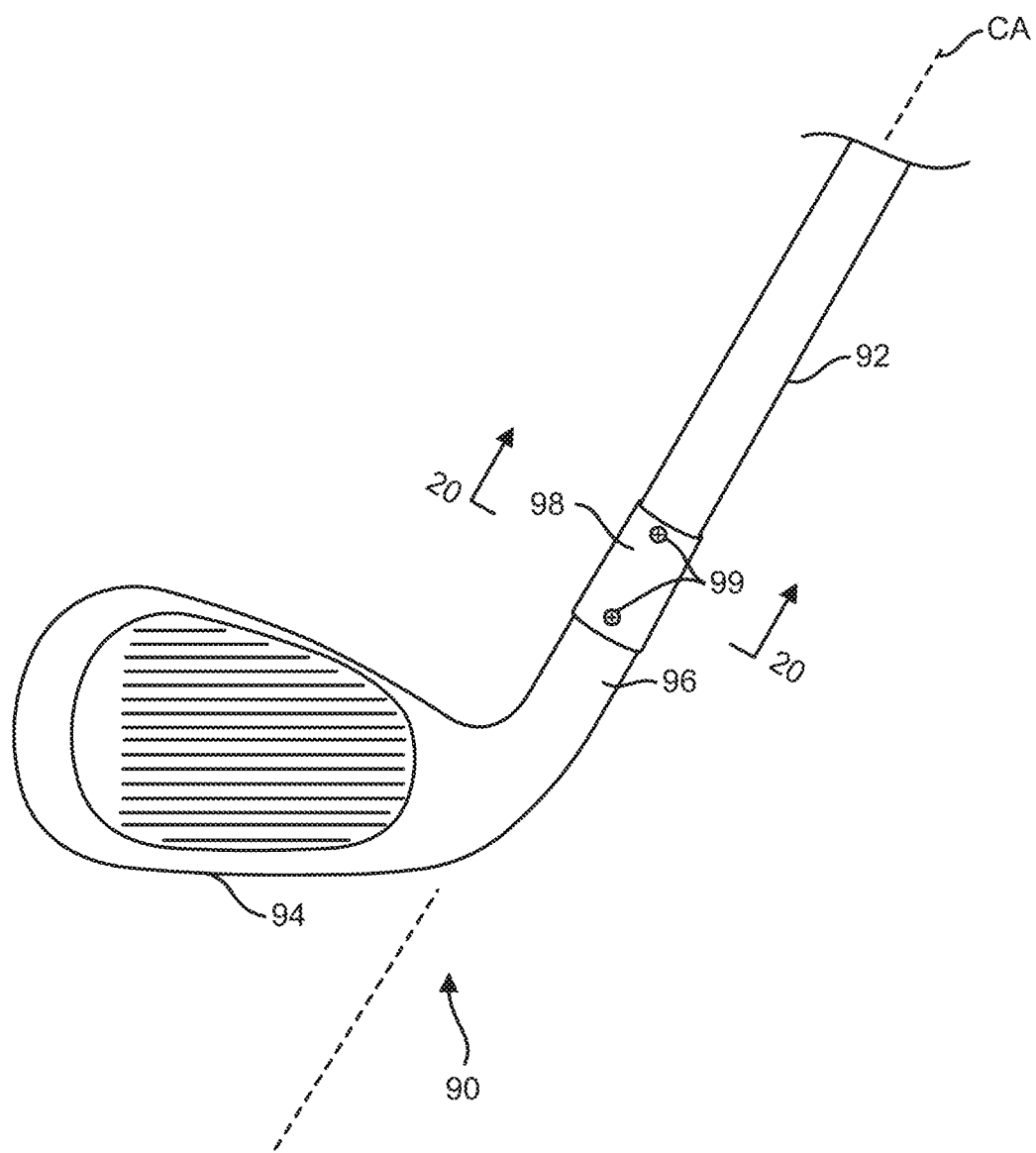
FIG. 19 is a fragmentary schematic illustration of a club head and a distal end segment of a shaft of a golf club.
Figure 20:
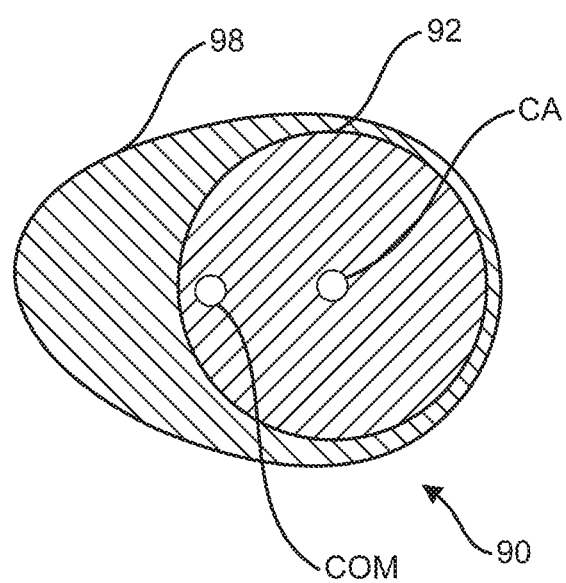
FIG. 20 is a schematic cross-sectional illustration of the golf club of FIG. 19 taken in the plane of line 20-20 of FIG. 19.

Referring to FIGS. 19 and 20, an adjustable golf club is generally indicated at reference number 90. The golf club 90 comprises a shaft 92 having a proximal end and a distal end spaced apart along a center axis CA. A club head 94 extends from the distal end of the shaft 92 and is attached to the shaft at a joint region of the shaft 96. An eccentric weight 98 is mounted on the shaft 92 for selective rotation about the center axis CA of the shaft with respect to the shaft. The eccentric weight 98 has a center of mass COM that is radially offset from the center axis CA of the shaft. Thus the weight 98 can be selectively rotated about the shaft 92 to adjust the balance and weight distribution of the club 90 to, for example, account for flaws in a golfer's swing. Suitably, the golf club 90 further includes a locking mechanism 99 for selectively locking the eccentric weight in the desired circumferential position about the center axis CA of the shaft 92. In the illustrated embodiment, the locking mechanism 99 comprises two set screws that are threadably engaged with the weight 98 and can engage the shaft 92 to fix the circumferential position of the weight with respect to the shaft. Other embodiments can use other locking mechanisms. In one embodiment, in addition or as an alternative to being rotatable about the shaft 92, the weight is selectively slidable along the length of the shaft to adjust the balance of the golf club 90.

Figure 21:
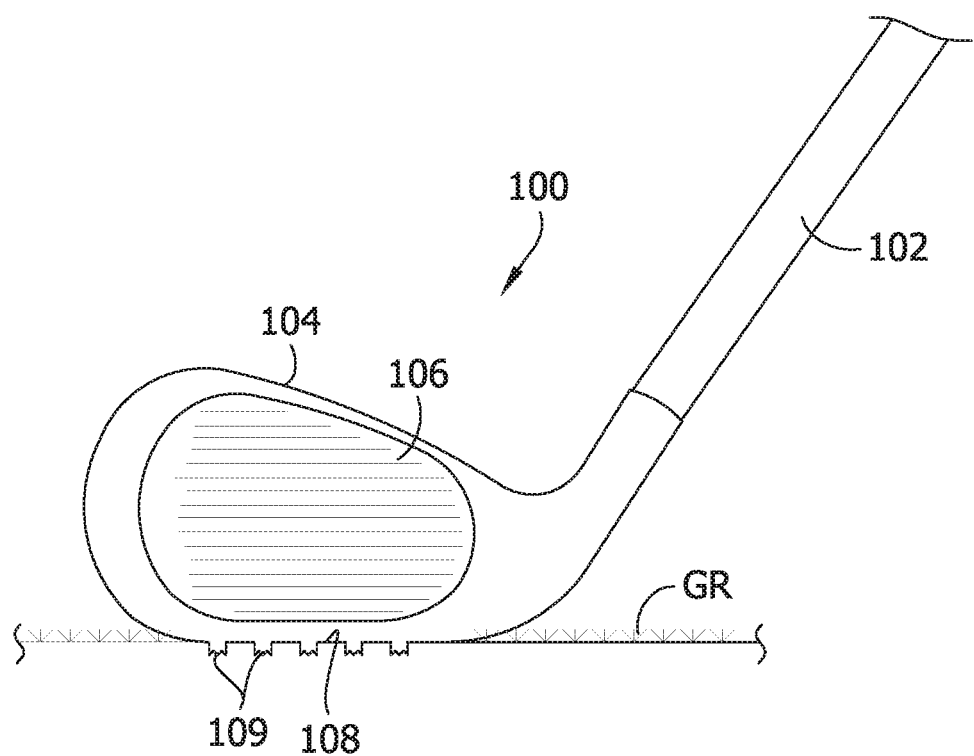
FIG. 21 a fragmentary schematic illustration of a club head and a distal end segment of a shaft of another embodiment of a golf club.

Referring to FIG. 21, another embodiment of a golf club is generally indicated at reference number 100. The golf club 100 comprises a shaft 102 having a proximal end and a distal end and a club head 104 mounted on the distal end of the shaft. The club head 104 includes a face 106 for striking a golf ball (not shown) supported on a ground region GR and a sole 108 for engaging the ground region as the golf club is swung to strike the golf ball. The sole 108 defines a traction formation 109 for creating enhanced friction between the sole and the ground region GR as the golf club 100 is swung to reduce the speed at which the club head 104 travels as the face 106 strikes the golf ball. In the illustrated embodiment, the traction formation 109 comprises a plurality of jagged protrusions extending from the sole 108 of the club head 104. Other traction formations (e.g., smooth protrusions, grit material, surface etching, grooves or ridges transverse to the swing path, fibrous additives, etc.) can also be used in other embodiments. Reducing the speed of the club head 106 at the point of ball strike is thought to enhance control of the golf club. Furthermore, the increased friction with the ground region GR is thought to enhance the tactile feedback provided to the golfer. Thus, the traction formations 109 may be particularly well-suited for finesse clubs such as pitching wedges. It is understood that the soles of other clubs may also be formed with traction formations in other embodiments.

Figure 22:
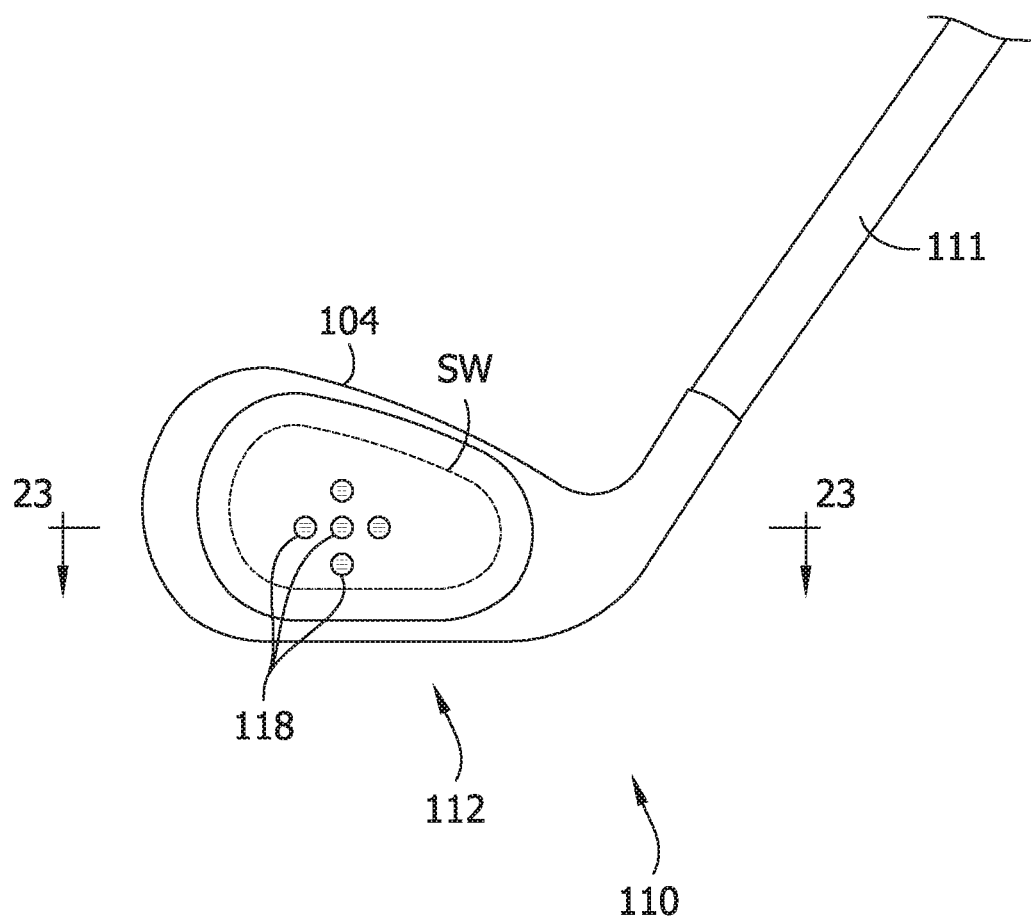
FIG. 22 is a schematic illustration of a club head and a distal end segment of a shaft of another embodiment of a golf club.
Figure 23:
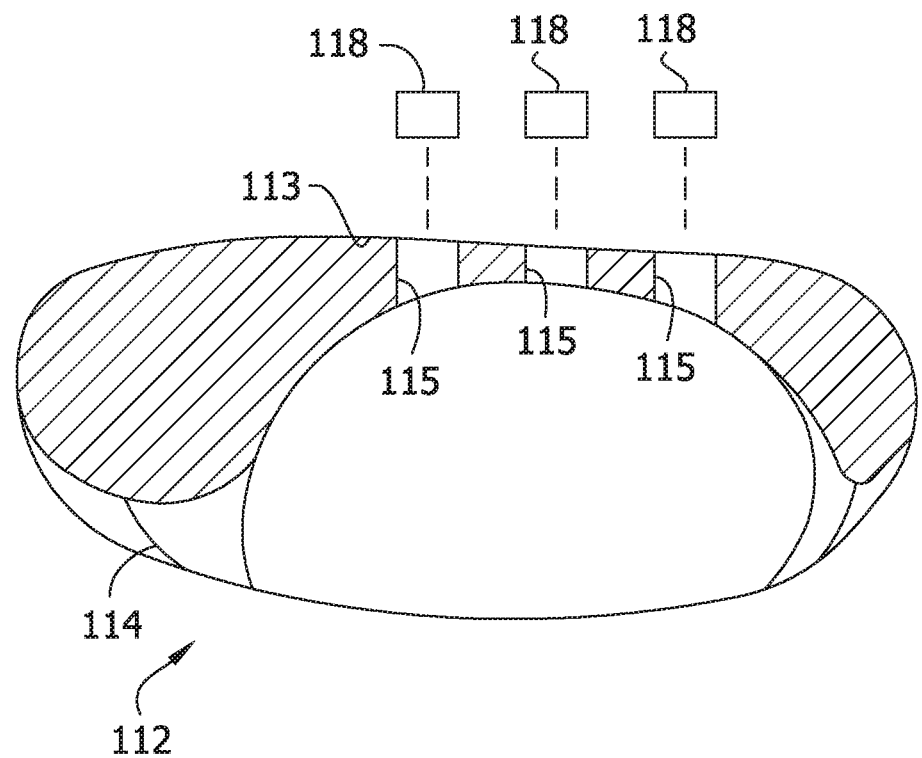
FIG. 23 is a schematic cross-sectional illustration of the golf club of FIG. 22 taken in the plane of line 23-23 of FIG. 22.

Referring to FIGS. 22-23, another embodiment of a golf club is generally indicated at reference number 110. The golf club 110 includes a shaft 111 and a club head, generally indicated at 112, mounted on the distal end of the shaft. As explained below, the club head 112 is configured to enhance the flexibility of a sweet spot region SW of the club head. The club head 112 has a face 113, a back 114, and a thickness extending between the face and the back. In the illustrated embodiment, the club head has a perimeter region that extends circumferentially around the sweet spot region SW. The thickness of the club head 112 is greater in the perimeter region than in the sweet spot region SW so that the club head preferentially flexes along the sweet spot region while the perimeter region provides the club head with the necessary strength. As shown in FIG. 23, the club head defines a plurality of holes 115 spaced apart along the face 113 and extending through the thickness of the club head. In the illustrated embodiment, the holes 115 are arranged at spaced apart locations in the sweet spot region SW. The holes 115 reduce the rigidity of the club head 112 in the sweet spot region to enhance flexibility. Though the holes 115 extend through the entire thickness of the club head 112 in the illustrated embodiment, in other embodiments the holes can extend through less than the entire thickness, e.g., from the face 113 through only a portion of the thickness. In the illustrated embodiment, the club head 112 is metal. A polymer plug 118 is received in each of the holes 115. The enhanced flexibility provided by the club head 112 as compared with conventional club heads is thought to enhance control and provide a more forgiving ball strike action.

Figure 24A:
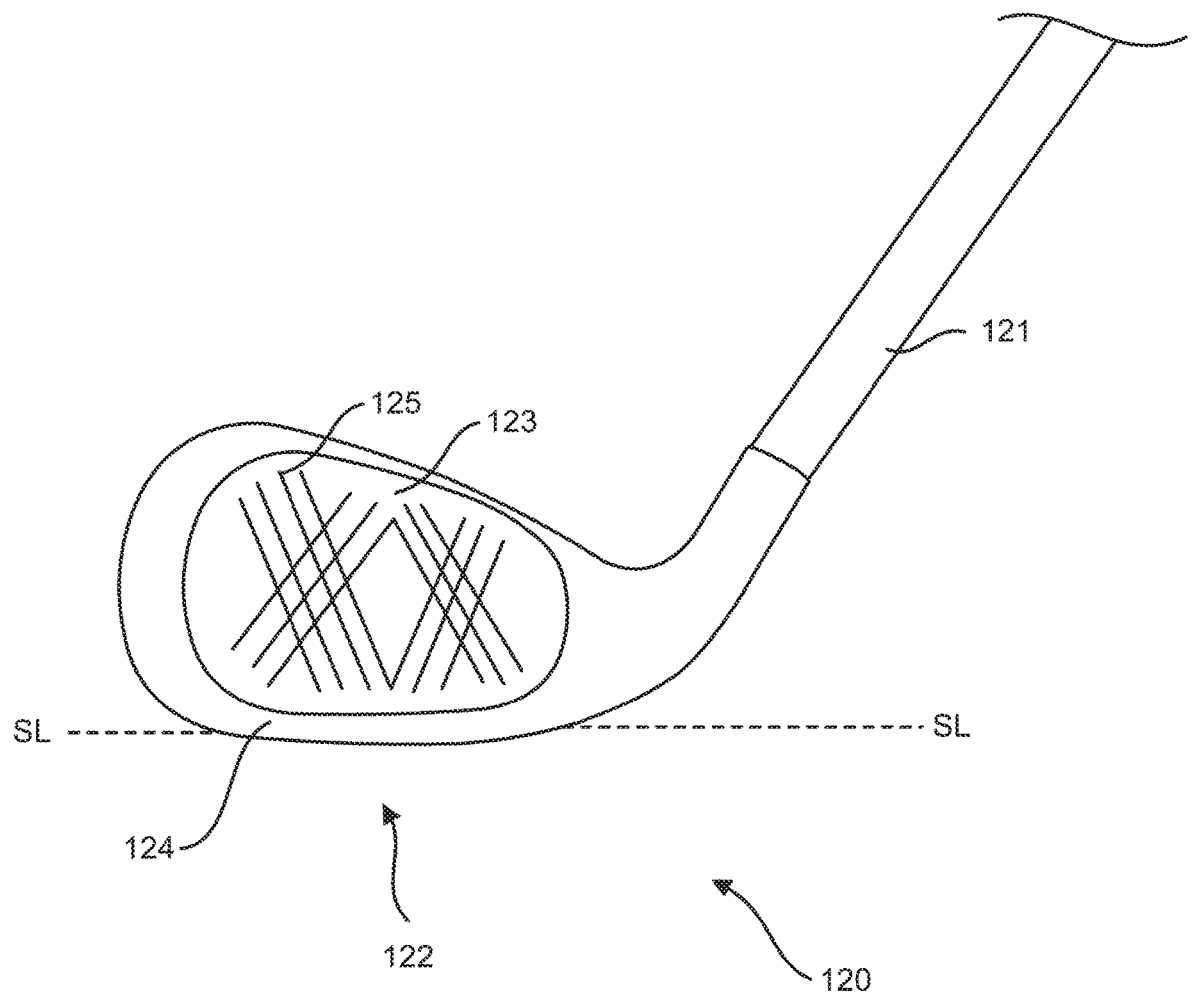
FIG. 24A is a schematic illustration of a club head and a distal end segment of a shaft of another embodiment of a golf club.
Figure 24B:
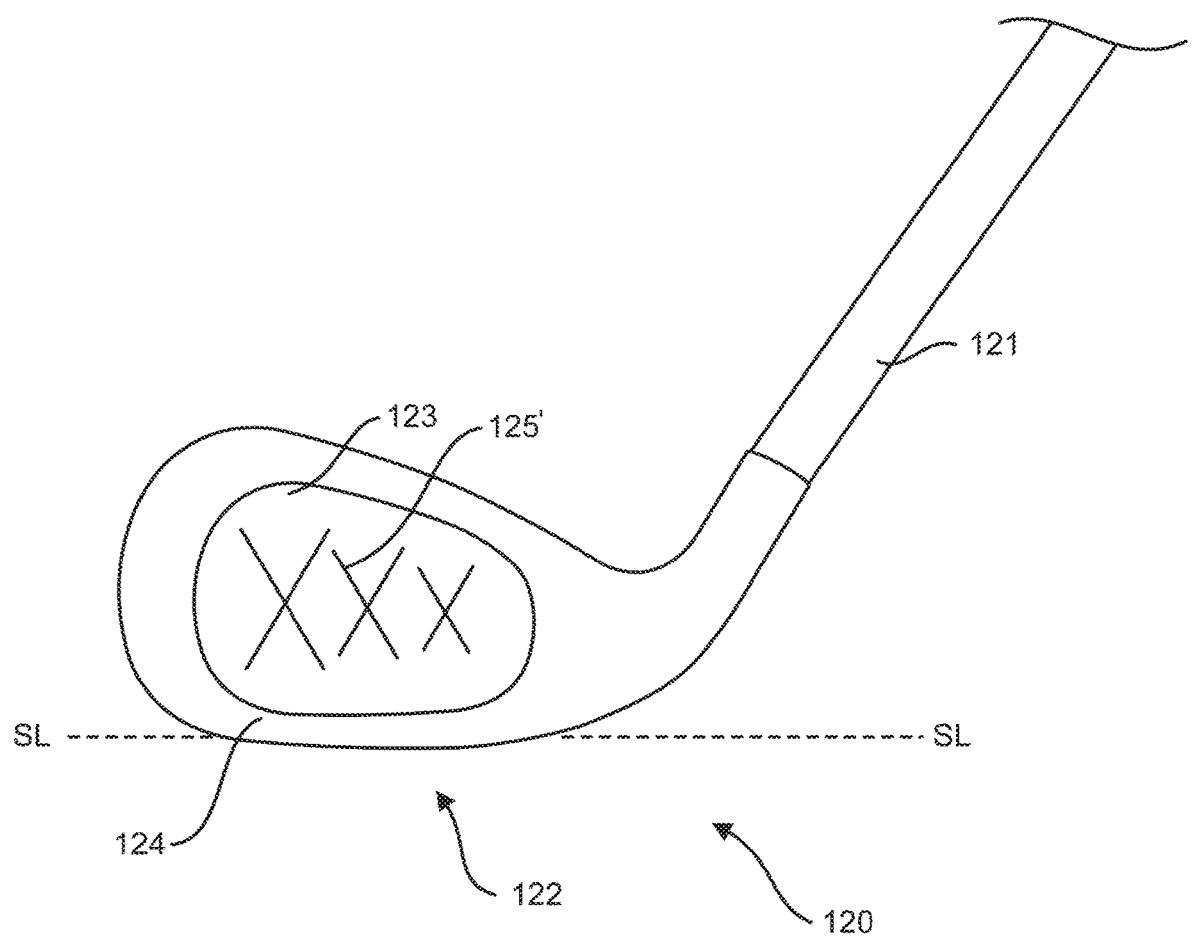
FIG. 24B is a schematic illustration of a club head and a distal end segment of a shaft of another embodiment of a golf club.
Figure 24C:
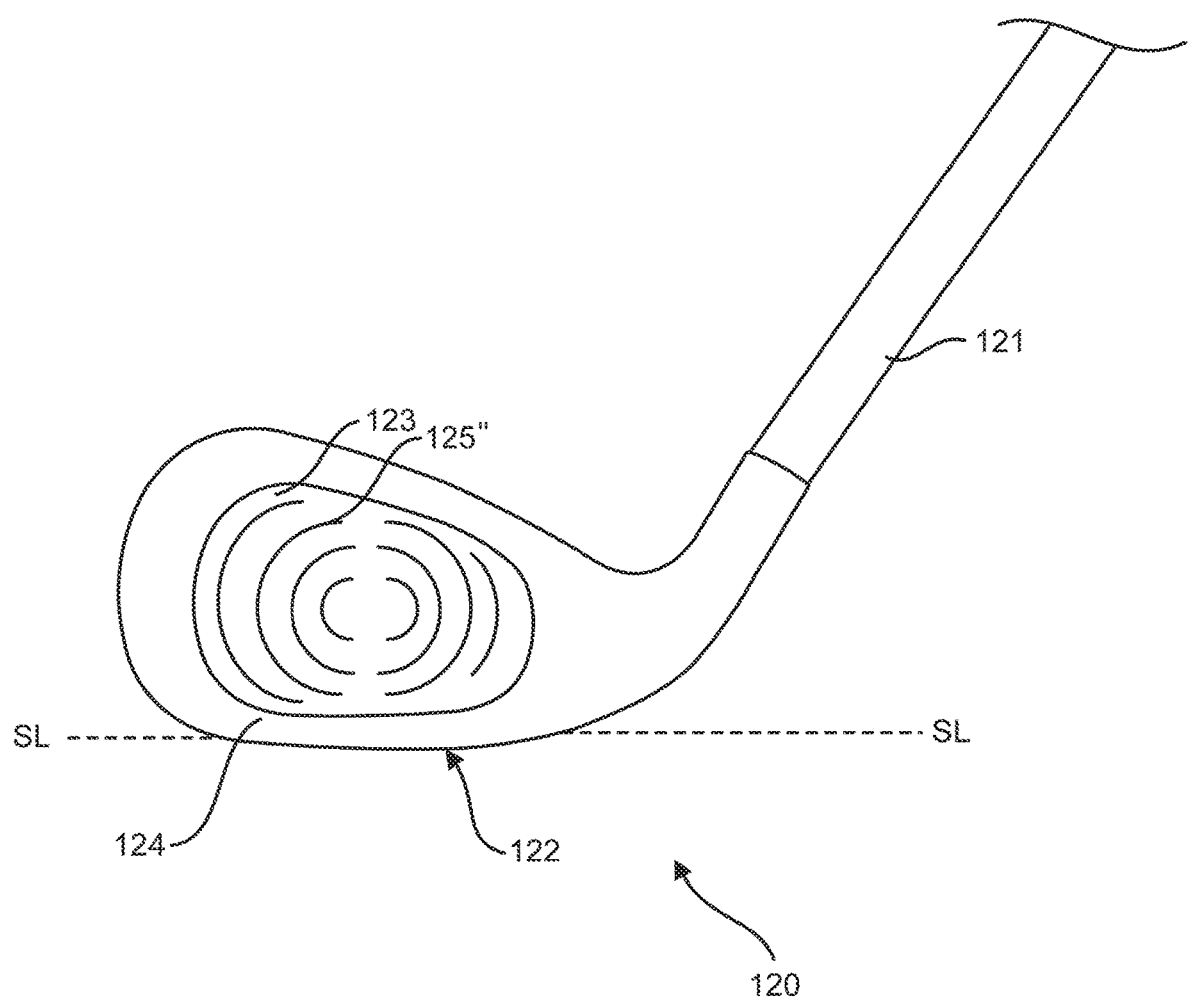
FIG. 24C is a schematic illustration of a club head and a distal end segment of a shaft of another embodiment of a golf club.
Figure 24D:
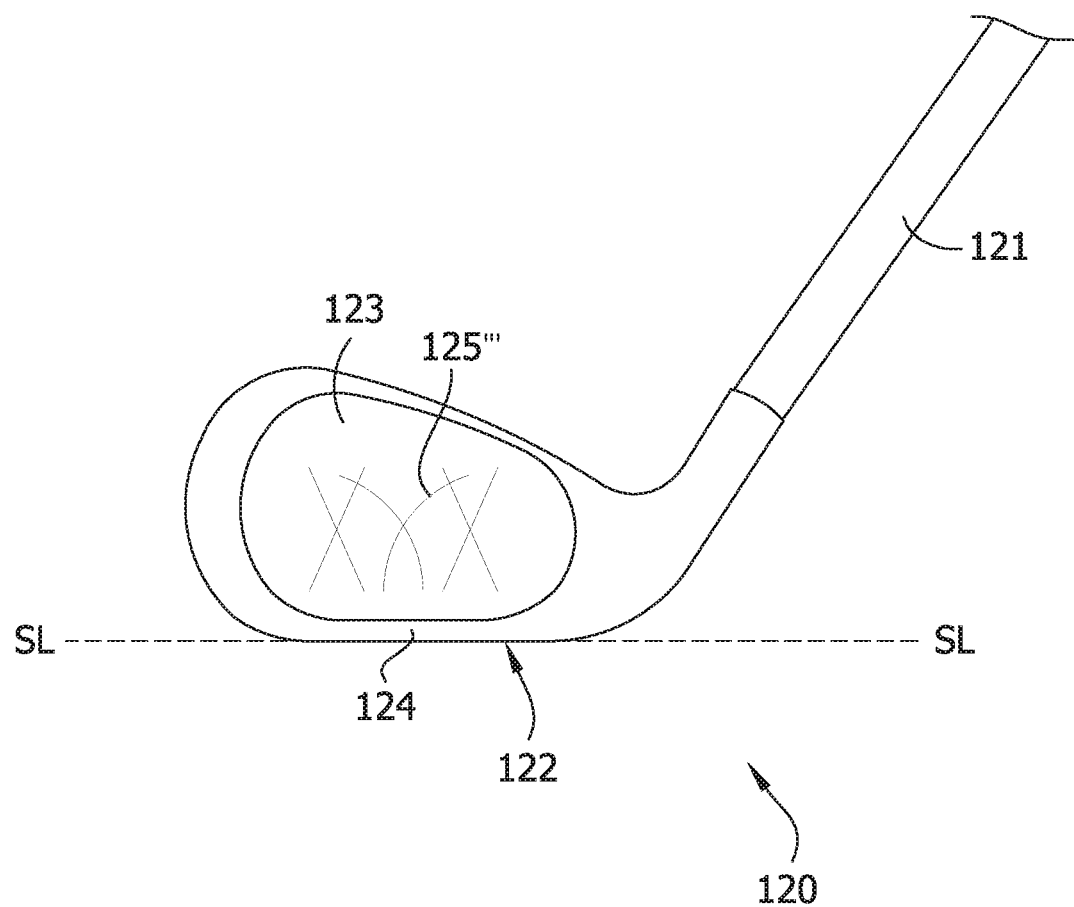
FIG. 24D is a schematic illustration of a club head and a distal end segment of a shaft of another embodiment of a golf club.

Referring to FIG. 24A-24D, other embodiments of a golf club are generally indicated at reference number 120. Each golf club 120 includes a shaft 121 and a club head, generally indicated at 122, mounted on a distal end of the shaft. The club head 122 has a face 123 having a top end margin and a bottom end margin. A sole 124 of the club extends rearwardly from the bottom edge margin of the face 123. The sole 124 also extends laterally along a sole line SL. The face 123 defines a plurality of elongate grooves 125, 125', 125'', 125'''. At least some of the elongate grooves 125, 125', 125'', 125''' are oriented transverse to the sole line SL to configure the club head 122 to have the desired flexibility in the sweet spot region. For example, in FIG. 24A, the elongate grooves 125 comprise a plurality of V-shaped grooves arranged in a spaced apart and nested arrangement and a plurality inverted V-shaped grooves arranged in a spaced apart and nested arrangement. In FIG. 24B, the elongate grooves 125' define a plurality of spaced apart X-shaped grooves. In FIG. 24C, the elongate grooves 125'' comprise a plurality of arcuate grooves arranged concentrically about a center point in the sweet spot region of the club head 122. In FIG. 25C, the elongate grooves 125''' comprise an arrangement of curved grooves and straight grooves extending along groove axes transverse to the sole line SL. Still other arrangements of grooves may be used in other embodiments. Further the transverse grooves of the club heads discussed in this paragraph may be combined with any of the features of the golf club of FIGS. 22-23 to further enhance the flexibility in the sweet spot region.

Figure 25:
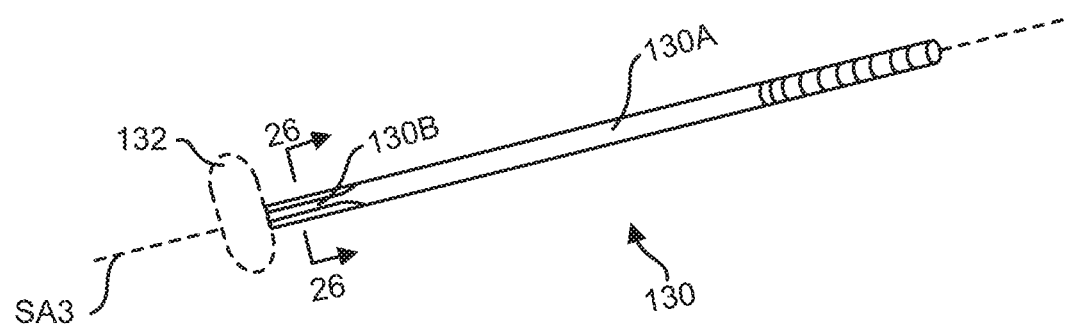
FIG. 25 is a schematic illustration of a shaft for a golf club and depicts a head of the golf club in broken line.
Figure 26:
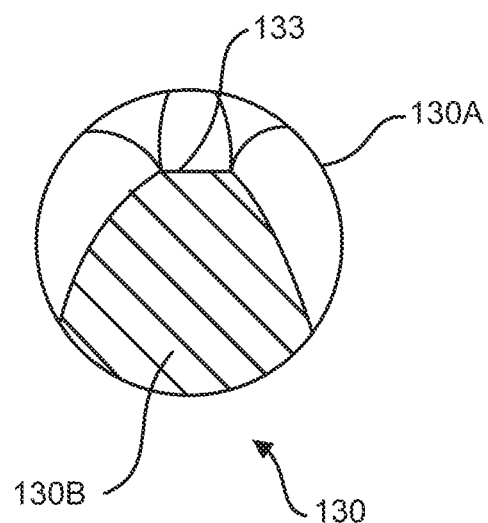
FIG. 26 is a schematic cross-sectional illustration of the shaft of FIG. 25 taken in the plane of line 26-26 of FIG. 25.

Referring to FIGS. 25-26. a shaft for a golf club is generally indicated at reference number 130. The shaft 130 has a proximal end, a distal end, and a length extending along a shaft axis SA3 between the proximal end and the distal end. A club head 132 is configured to be mounted on the distal end of the shaft 130. The shaft 130 includes a main segment 130A extending distally along the shaft axis SA3 from the proximal end to a distal end of the main segment. The main segment 130A has a cross-sectional shape in a plane orthogonal to the shaft axis SA3 that is substantially round (e.g., circular, oval, etc.). The shaft 130 also includes a flex control segment 130B. The flex control segment 130B extends distally along the shaft axis SA3 from adjacent the distal end of the main segment 130A toward the distal end of the shaft. In the illustrated embodiment, the flex control segment 130B forms a distal end segment of the shaft, but in other embodiments, the flex control segment could comprise a segment that is spaced apart from the distal end of the shaft. The flex control segment 130B has a cross-sectional shape in a plane orthogonal to the shaft axis SA3 that includes a flat side 133. The cross-sectional shape of the flex control segment 130B causes it to flex differently than the main segment 130A as the shaft 130 is swung. Specifically, the flex control segment 130B is more flexible than the main segment 130A in certain radial bending directions. Thus, swing outcomes may be adjusted without adjusting a golfer's swing by changing the circumferential orientation of the flat side 133 with respect to the club head. It is understood that the flex control segment 130A could have any cross-sectional shape that is suitable for inducing the desired flexure of the shaft 130 during swinging and is not limited to the cross-sectional shape illustrated in FIG. 26.

Figure 27:
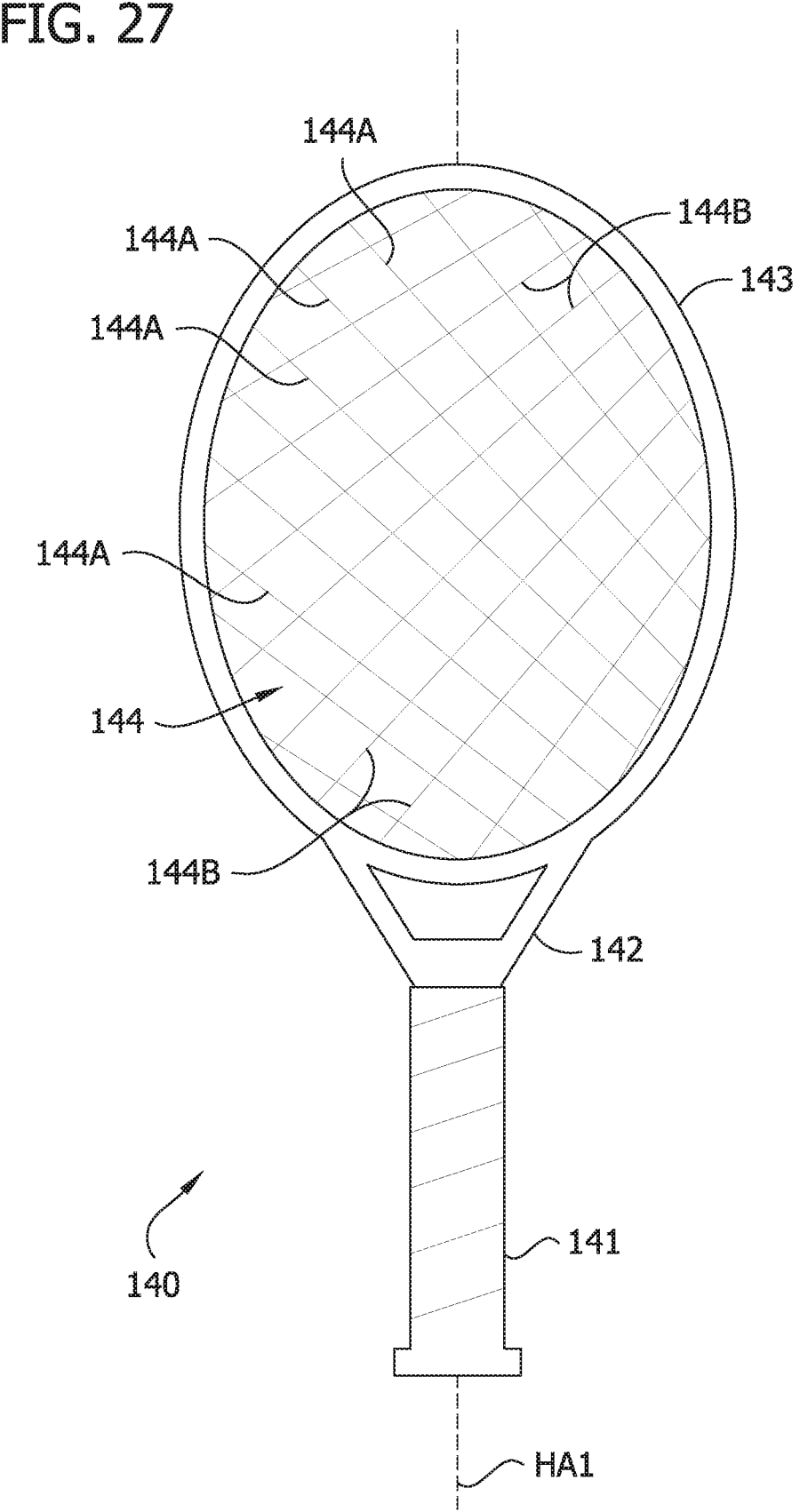
FIG. 27 is a schematic illustration of a racket.

Referring to FIG. 27, a racket for use in a racket sport such as tennis, racquetball, badminton, squash, etc. is generally indicated at reference number 140. The racket 140 has a handle 141 having an axis HAL a neck 142 extending from a distal end of the handle, and a head 143 supported on the neck. The head 143 has a perimeter and defines a plurality of string holes configured to receive one or more strings 144 strung through the head to form a weave. The strings 144 are woven to include a plurality of warp segments 144A and a plurality of weft segments 144B that are woven in a weave pattern configured to augment effects imparted on a ball, shuttlecock, or the like, when struck by the racket 140. For example, in one embodiment, the racket 140 comprises a tennis racket, and the strings 144 are woven in a weave pattern configured to augment spins imparted on a tennis ball. Each of the warp string segments 144A comprises a skewed segment extending along a respective skew axis. The skew axes of the illustrated warp string segments 144A are each oriented at a different skew angle with respect to the handle axis HA1. Each of the weft string segments 144B is oriented transverse to the warp segments 144A and comprises a skewed segment extending along a respective skew axis. The skew axes of the illustrated weft string segments 144B are each oriented at a different skew angle with respect to the handle axis HA1. In other embodiments, some of the warp and weft segments may be oriented at the same skew angle and/or a non-skewed angle.

Figure 28:
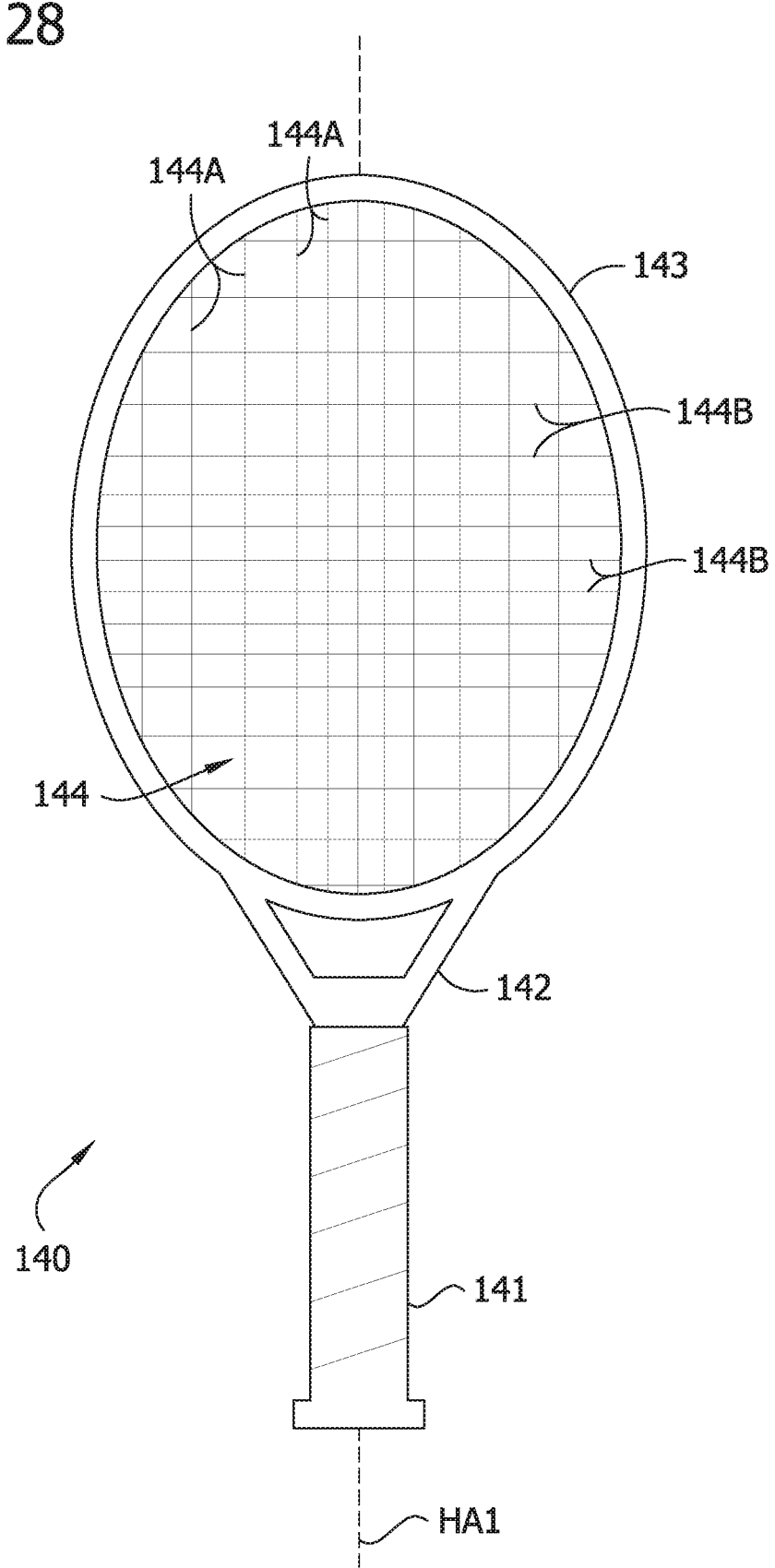
FIG. 28 is a schematic illustration of another racket.

For example, referring to FIG. 28, in one embodiment, the warp string segments 144A are each oriented substantially parallel to the handle axis HA1 and the weft string segments 144B are each oriented substantially perpendicular to the handle axis. Instead of weaving the string segments to extend along skew axes, the illustrated strings 144 are woven in a weave pattern that includes a perimeter region having a relatively loose or open weave, an inner region having a relatively tight or closed weave, and an intermediate region having a weave that is more open than the inner region but less open than the perimeter region. The warp segments 144A comprise unequally spaced segments extending along a vertical axis (e.g., an unequally spaced string axis) at spaced apart positions along a horizontal axis (e.g., a spacing axis) such that each adjacent pair of the warp segments is spaced apart by a spacing distance extending along the horizontal axis and the spacing distances decrease as the distance from the perimeter of the head along the spacing axis increases. Similarly, the weft segments 144B comprise unequally spaced segments extending along the horizontal axis (e.g., an unequally spaced string axis) at spaced apart positions along the vertical axis (e.g., a spacing axis) such that each adjacent pair of the weft segments is spaced apart by a spacing distance extending along the vertical axis and the spacing distances decrease as the distance from the perimeter of the head along the spacing axis increases. It is understood that the spacing of adjacent warp and weft segments 144A, 144B may vary in other ways to configure the racket 140 to impart the desired effects on the ball or shuttlecock.

Figure 29:
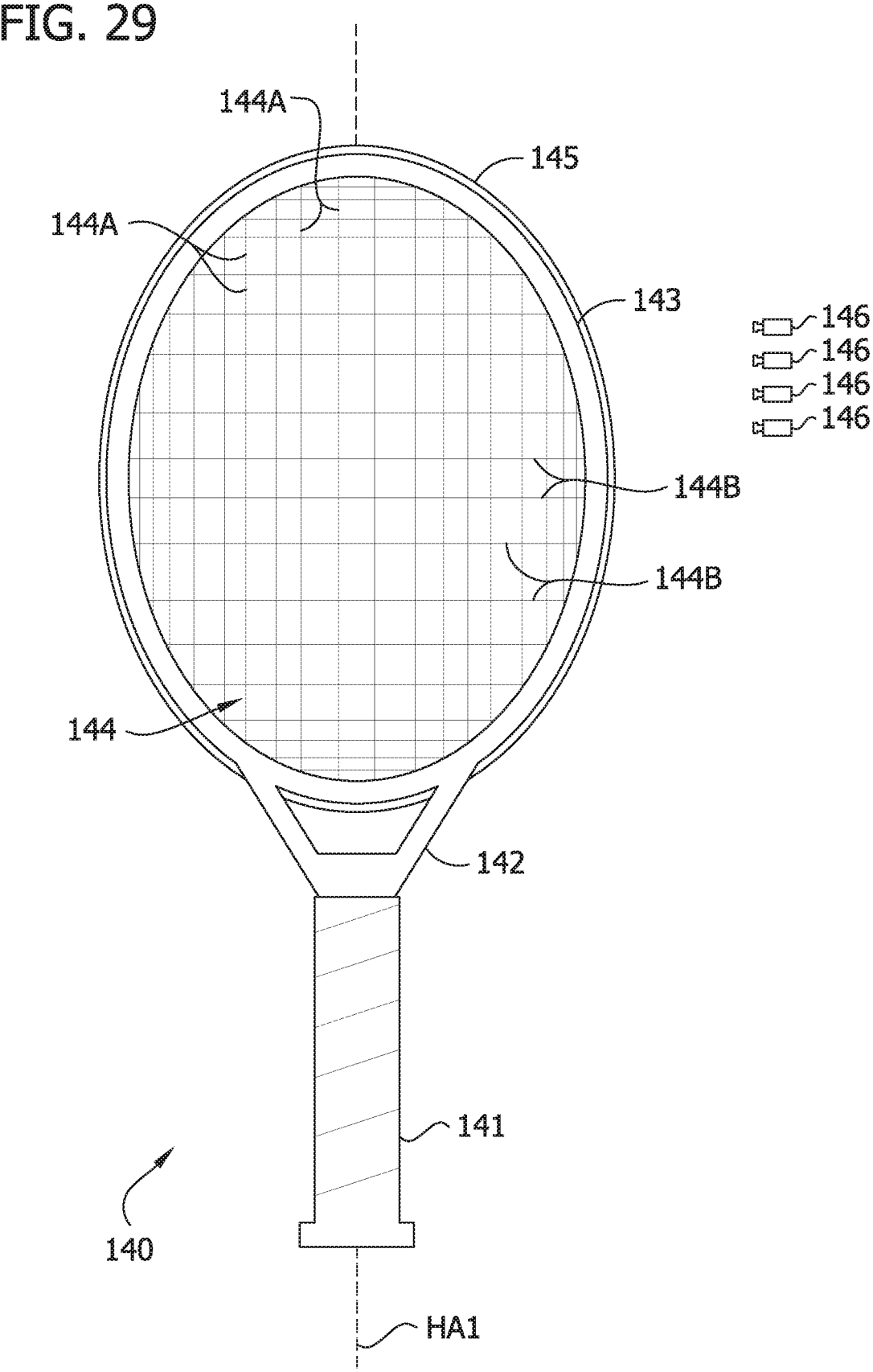
FIG. 29 is a schematic illustration of another racket.

Referring to FIG. 29, in certain embodiments, the racket 140 can be configured in other ways to impart the desired effects on the ball or shuttlecock during game play. For example, instead of adjusting the spacing of the warp and weft string segments 144A, 144B, the tension in selected ones of the string segments can be adjusted. For example, some of the string segments 144A, 144B of the head 143 are strung to have greater tension than others of the string segments. The tension imparted on each string segment 144A, 144B can be selected to impart the desired effects on the ball or shuttlecock during game play.

In addition, the racket 140 shown in FIG. 29 includes a balancing track 145 (broadly, a weight mount) extending around the perimeter of the head 143. the balancing track 145 defines a mounting groove configured to mount a selected number of balancing weights 146 at desired circumferential positions about the perimeter of the head 143. The illustrated weights 146 include mounting tongues that are configured to snap into the groove of the track 145 to mount the weight at the desired position. In other embodiments, weight mounts may have other configurations and may be configured to mount weights at other locations on the frame of the racket 140. By mounting the weights 146 at the desired positions around the perimeter of the head 143, the balance of the racket 140 can be adjusted to alter the results of a swing produced by a player's existing swing mechanics. In addition, the weights may be used as a training method to correct errors in swing mechanics over time by rebalancing the racket and forcing the player to compensate.

Helmets are used in various sports to protect the player from head injuries. Typical helmets have rigid shells or exoskeletons that are the first point of impact during use. Such rigid shells are typically formed of a smooth material that limits friction on impact, which could otherwise cause movement of the head and helmet to slow while momentum causes the body to move relative to the head, causing further injury. However, conventional rigid shells do not dampen the forces imparted on the helmet at the point of impact.

Figure 30:
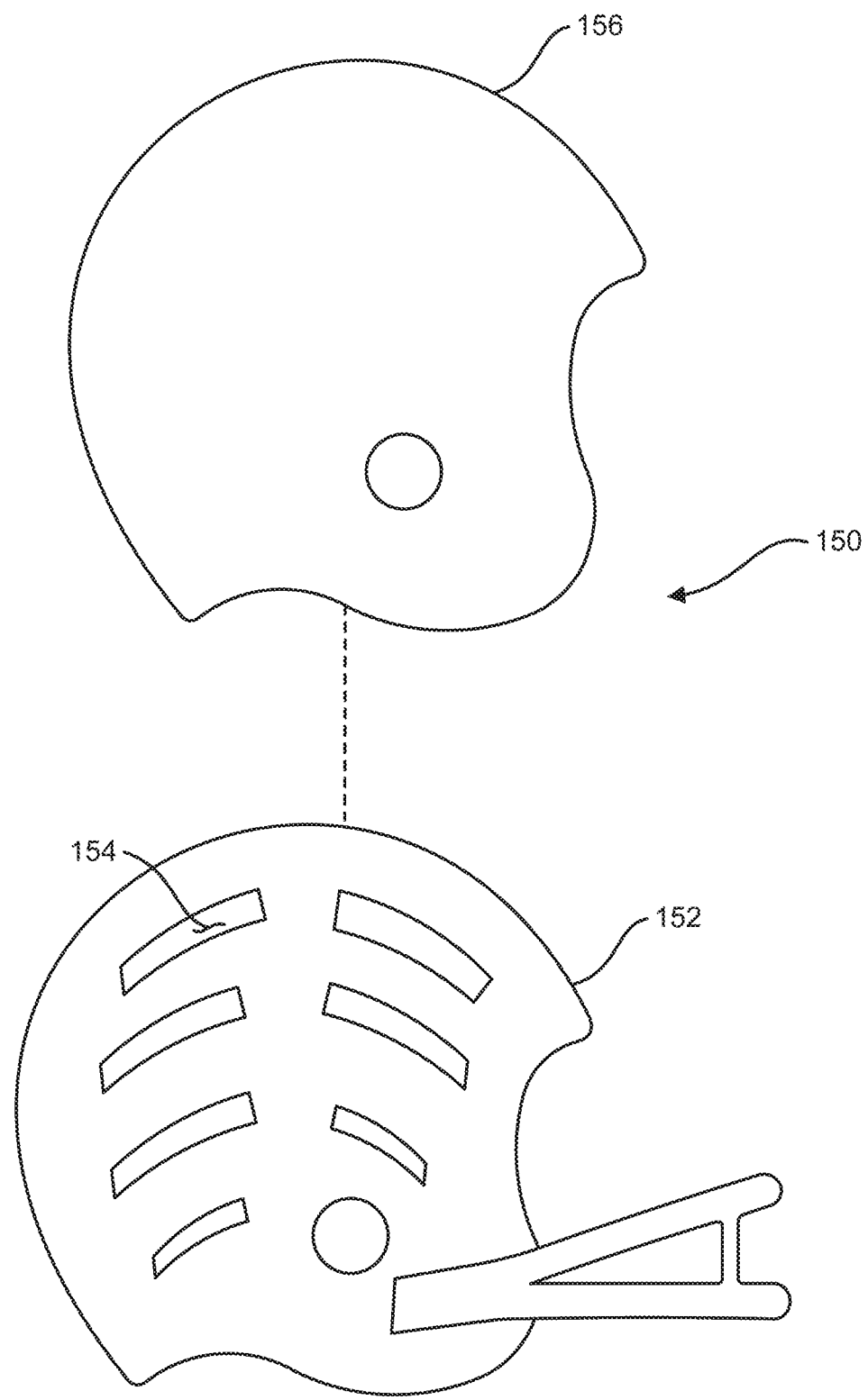
FIG. 30 is a schematic exploded illustration of a helmet.

Referring to FIG. 30, one embodiment of a helmet is generally indicated at reference number 150. The helmet 150 comprises a rigid skeleton 152 having an exterior side and an interior side defining a cavity for receiving a head of a user. In certain embodiments, the deformable padding is placed on the interior side of the skeleton 152 so that the interior of the helmet comfortably conforms to the head of the user. The skeleton 152 defines a plurality of holes 154 extending from the interior side through the exterior side for circulating air between the outside and inside of the helmet. The helmet further comprises a layer of deformable padding 156 that extends over the exterior side of the skeleton 152. In one embodiment, the padding comprises a deformable material having a low coefficient of friction, such as polyurethane. Other materials may also be used in other embodiments. Suitably, the padding 156 defines a continuous and smooth exterior surface that has a low coefficient of friction. The padding 156 can be attached to the skeleton 154 in any suitable manner. In one embodiment, the padding 156 is molded directly onto the skeleton 152. Suitably, the padding 156 can have a variable porosity. As compared to a helmet with a rigid outer shell, the helmet 150, with its deformable outer padding 156, is thought to reduce the deceleration rate of the helmet on impact and thus limit head injuries due to impact. In other embodiments, a deformable padding may be formed over other protective garments such as shoulder pads, knee pads, knee braces, etc.

When a head injury occurs during a sporting event, it is important to quickly determine whether the injury caused a concussion. Various testing protocols have been developed. Typically, these involve various tests of cognition, including memory tests, optical response tests, vestibular testing, etc. However, the results of the testing may be adversely affected by the injured being distracted by gameplay taking place in close proximity, by crowd noise, etc.

Figure 31:
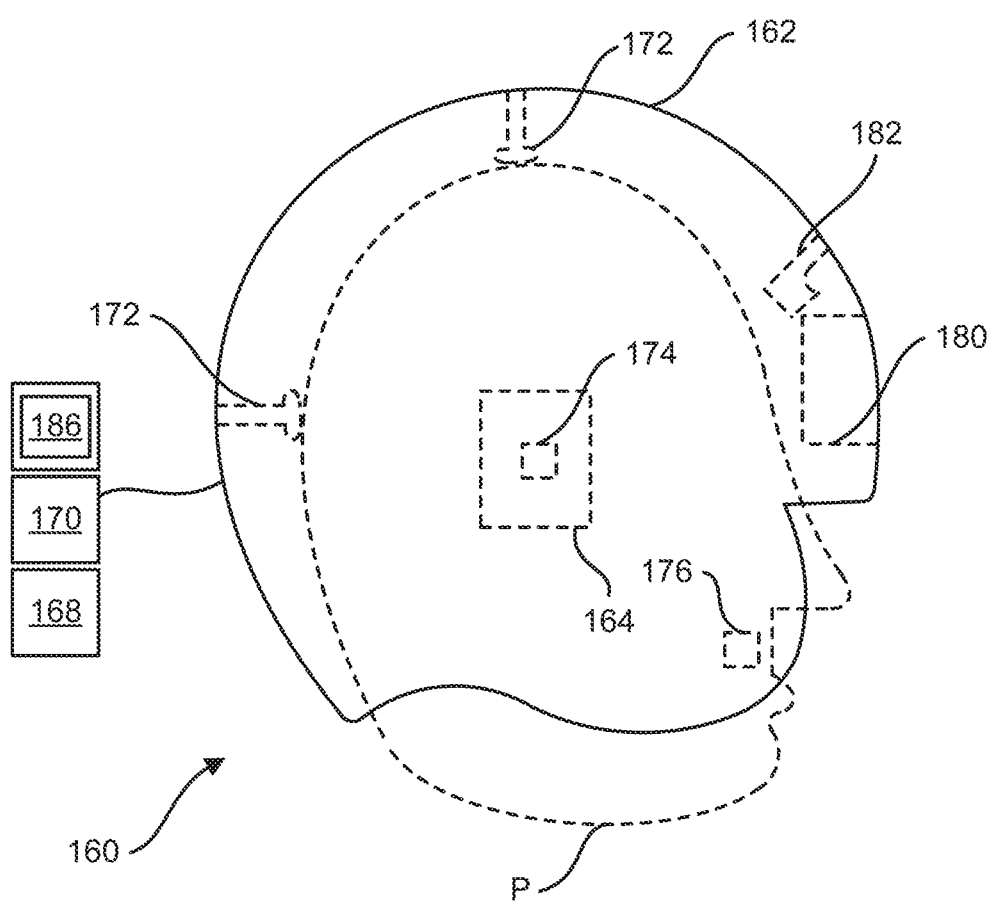
FIG. 31 is a schematic illustration of a concussion testing system.

Referring to FIG. 31, one embodiment of a system for evaluating whether a person P has sustained a concussion is generally indicated at 160. The testing system 160 includes a headset or mask 162 configured to be worn by the injured person P. The headset 162 is configured to limit at least one of environmental noise (broadly, an environmental acoustic stimulus) and visual distractions (broadly, an environmental optical stimulus) when the headset is worn by the person P. In the illustrated embodiment, the headset 162 is configured to cover both the eyes and ears of the person wearing the headset to limit both environmental acoustic stimuli and environmental visual stimuli that reaches the person P.

The testing system 160 includes diagnostic transmitters configured to transmit a diagnostic signal to the person P. In the illustrated embodiment, one of the diagnostic transmitters is an acoustic transmitter 164, such as a speaker. The acoustic transmitter 164 is configured to transmit acoustic signals to the ears of the person P when the headset 162 is worn by the person. Suitably, the testing system 160 can include left and right acoustic transmitters that separately convey acoustic signals to the left and right ears of the person. In the illustrated embodiment, the testing system 160 includes a memory 168 for storing acoustic signal data and a controller 170 operatively connected the memory and to the acoustic transmitter to selectively transmit the acoustic signals stored in the memory using the acoustic transmitter. For example, the memory 168 may store audio files containing questions that the controller selectively transmits to the person P using the transmitter 164. The memory 168 can also include audio files containing various acoustic tones that the controller 170 selectively plays to the left and right ears of the person using the acoustic transmitters 164. In other embodiments, no memory is required and instead the acoustic transmitter is configured to transmit acoustic tones whose volume and pitch is controlled by the controller 170.

The illustrated testing system 160 includes several diagnostic sensors configured to sense the response of the person to the person P to the acoustic signals. For example, the illustrated testing system includes electrodes 172 configured to detect brainwave activity in response to the acoustic signals (e.g., an automated auditory brainstem response). The electrodes 172 are configured to transmit a signal representative of the detected brainwave activity to the controller, which functions as a cognitive response analyzer, analyzing the brainwave activity signal (broadly, cognitive response signal) and evaluating whether the person sustained a concussion based in part on the analysis of the brainwave activity. In addition to the electrodes 172, the illustrated testing system includes left and right otoacoustic emissions sensors 174 that are aligned with the left and right ears for sensing the sound waves generated in the inner ear in response to the acoustic signals. Each sensor 174 is configured to transmit a sound wave emissions signal to the controller 170, and the controller 170 is configured to analyze the signal and use the analysis to evaluate whether the person has sustained a concussion. Furthermore, the illustrated testing system 160 includes a microphone 176 configured to sense sound from the person, and in particular, the person's speech. The microphone 176 is configured to transmit signals representative of the sounds from the person P to the controller 170, and the controller is configured to analyze the signals to evaluate whether the person has sustained a concussion. In one embodiment, the sounds include answers to questions transmitted to the user via the transmitters 164. The controller 170 can be configured to compare the answers given by the user during the concussion test to previous answers provided by the same user that are stored in the memory 168 to the same questions to detect slurring of speech, reduced cognition, etc., which may provide indications of a concussion.

In addition to the acoustic transmitter 164, the illustrated testing system 160 also includes an optical diagnostic transmitter 180 configured transmit optical signals to the eyes of the person. In one embodiment, the optical transmitter 180 comprises a display. Other optical transmitters, such as lasers, etc., can also be used in other embodiments. Suitably, the controller 170 is operatively connected to the optical transmitter 180 for controlling the optical transmitter to transmit optical signals according to diagnostic routines stored in the memory 168. For example, the optical diagnostic routine may be configured to perform, for example, a nystagmus test (e.g., a horizontal gaze nystagmus test) by moving a display object horizontally across the field of view of the person P. Other types of optical signals can be provided in other embodiments. The testing system further includes an ocular response sensor 182 (e.g., a camera) configured to sense the ocular response (e.g., pupillary response) of the person to the optical signals transmitted on the display 180. The sensor 182 can convey an image signal or another cognitive response signal to the controller 170, which analyzes the signal to evaluate whether the person has sustained a concussion. In other embodiments, other sensors (e.g., brainwave sensors, etc.) can be used to detect a person's response to the optical signals.

The testing system 160 can be used with various testing protocols. For example, in one embodiment, acoustic and optical diagnostics are performed while the person P is instructed to balance on one leg, on a balance board, a pneumatic system that selectively adjusts the standing position of the person's legs, etc. In addition, the testing system 160 can be used to evaluate a concussion recovery by performing the same diagnostic testing at predetermined intervals after initial testing indicated a concussion was sustained. The controller 170 can be configured to provide indications of the results of its evaluation on a local display 186 or to transmit a signal including the results to another device (e.g., wirelessly via RF, Wi-Fi, etc.). In one embodiment, the controller 170 and the display 186 operate on a single device such as a laptop computer, a tablet, a smartphone, etc. The controller 170 could be configured to grade the severity of the concussion or provide an assessment of the likelihood that a concussion occurred. For sports leagues, each of the players may be required to record a baseline healthy response to the concussion diagnostics prior to gameplay at a time when the player is healthy. The baseline response is stored in the memory 168 and the controller 170 compares post-injury response to the baseline response to evaluate whether a concussion was sustained.

Although the illustrated testing system 160 is configured for acoustic and optical diagnostics other systems can include other diagnostics. For example, some systems will have only one of an acoustic and an optical system. Some systems, will include other testing systems such as kinesthetic testing (e.g., fine motor testing, gross motor testing, upper or lower extremity movement testing, etc.) taste/smell response testing, verbal and non-verbal mental acuity testing, etc.

To maintain sterility in a medical treatment facility such as a hospital, certain garments that come into close proximity or contact with a patient are regularly disposed of or replaced so that they can be sterilized. This process consumes both time and resources.

Figure 32:
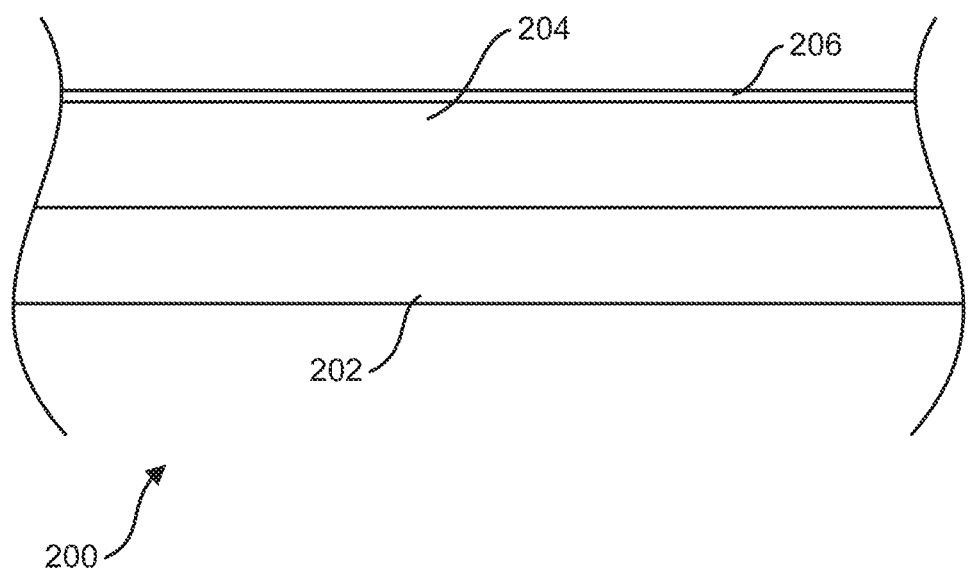
FIG. 32 is a schematic cross-sectional illustration of a garment material.

Referring to FIG. 32, a material for forming a garment for being donned by a practitioner while treating multiple patients is generally indicated at reference number 200. The material 200 may be used in various garments such as gloves, shoe covers, gowns, shirts, pants, body suits, face masks, etc. As will be explained below, garments formed of the material 200 can be sterilized while being worn by the practitioner so that the practitioner does not have to replace or dispose of the garment between visits with different patients. When the material 200 is formed into the garment, the garment comprises a body defining a cavity having an enclosed perimeter portion for receiving a body part of the practitioner. For example, a glove defines a cavity for receiving a hand, and a portion of the cavity is surrounded by the glove material; this portion can be referred to as the enclosed perimeter portion of the cavity. The material 200 includes a first layer 202 that is substantially UV-opaque. In one embodiment the material of the first layer 202 is non-latex. When the material 200 is formed into the garment, the UV-opaque layer can define an interior layer of the garment that extends around substantially the entire enclosed perimeter portion of the cavity. In addition, the material 200 includes a layer 204 that is substantially nonporous. In one embodiment, the nonporous layer 204 is at least somewhat UV-transmissive. In the assembled garment, the nonporous layer extends around the entire enclosed perimeter portion of the cavity and is positioned on the exterior of the UV-opaque layer.

In use, a garment formed using the material 200 can be sterilized between patients without being disrobed from the practitioner. For example, the garment and the body part donning the garment can be inserted into a UV sterilization chamber that directs UVC light to the garment. The UVC light penetrates the outer, non-porous layer 204 and sterilizes the layer but does not penetrate the garment to the practitioner because the UV-opaque layer does not transmit the UVC light. Moreover, because the layer 204 is nonporous, it protects the UV-opaque layer 202 from becoming desterilized. The sterilizing UV light therefore does not need to penetrate the UV-opaque layer to penetrate the garment. In addition to using UVC light to sterilize the material 200, in some embodiments other sterilization techniques can also be employed. For example, the garment may be washed using an alcohol, a detergent, a soap, etc. In addition, a sterile coating 206 (e.g., an antibacterial film) may be applied over the exterior surface of the material 200 at manufacturing and/or during sterilization. In some embodiments, rather than forming a premanufactured garment, the material 200 may be provided to a practitioner in bulk or raw form and wrapped around the desired body part prior to use (e.g., as a shrink wrap, etc.). In some embodiments, the UV-opaque layer 202 or another layer disposed between the UV-opaque layer and the nonporous layer 204 (not shown) is configured to fluoresce or glow under UVC light to indicate when a tear, pinhole, or other opening has formed in the nonporous layer, at which time the garment is spent and must be disposed of. In some embodiments 200 the material is self-sealing when heated. It is particularly contemplated that garments formed from the material 202 can be used by the patients and/or families of patients who are stationed in in infection control or ICU environment.

A method of treating multiple patients with a garment formed of the material 200 will now be briefly described. Initially, the practitioner removes the garment from sterile packaging and dons the sterile garment. The practitioner then contacts a first patient with the sterile donned garment to treat the first patient. The contact with the first patient desterilizes the garment. Subsequently, the practitioner re-sterilizes the donned desterilized garment without disrobing by inserting the desterilized garment into a sterilization chamber. In one embodiment the sterilization chamber is formed in a housing of sterilization system. The system further includes a UV light scanner configured to automatically direct UVC light over the entire exterior surface of the garment. For example, the practitioner may position the donned garment in the chamber for a predetermined period of time or until the system provides an indication that sufficient quantities of UVC light have been directed over the exterior surface of the garment to fully sterilize the garment. In some embodiments, the system also includes a movable spray head that automatically sprays the entire exterior surface of the garment with a sterilization spray (e.g., alcohol, an antiseptic, etc.) as or after the scanner directs UV light over the garment. The donned garment is removed from the chamber when the sterilization process is complete. The practitioner can then contact a second patient with the re-sterilized donned garment to treat the second patient. This process may be repeated throughout the working day of the practitioner.

Figure 35:
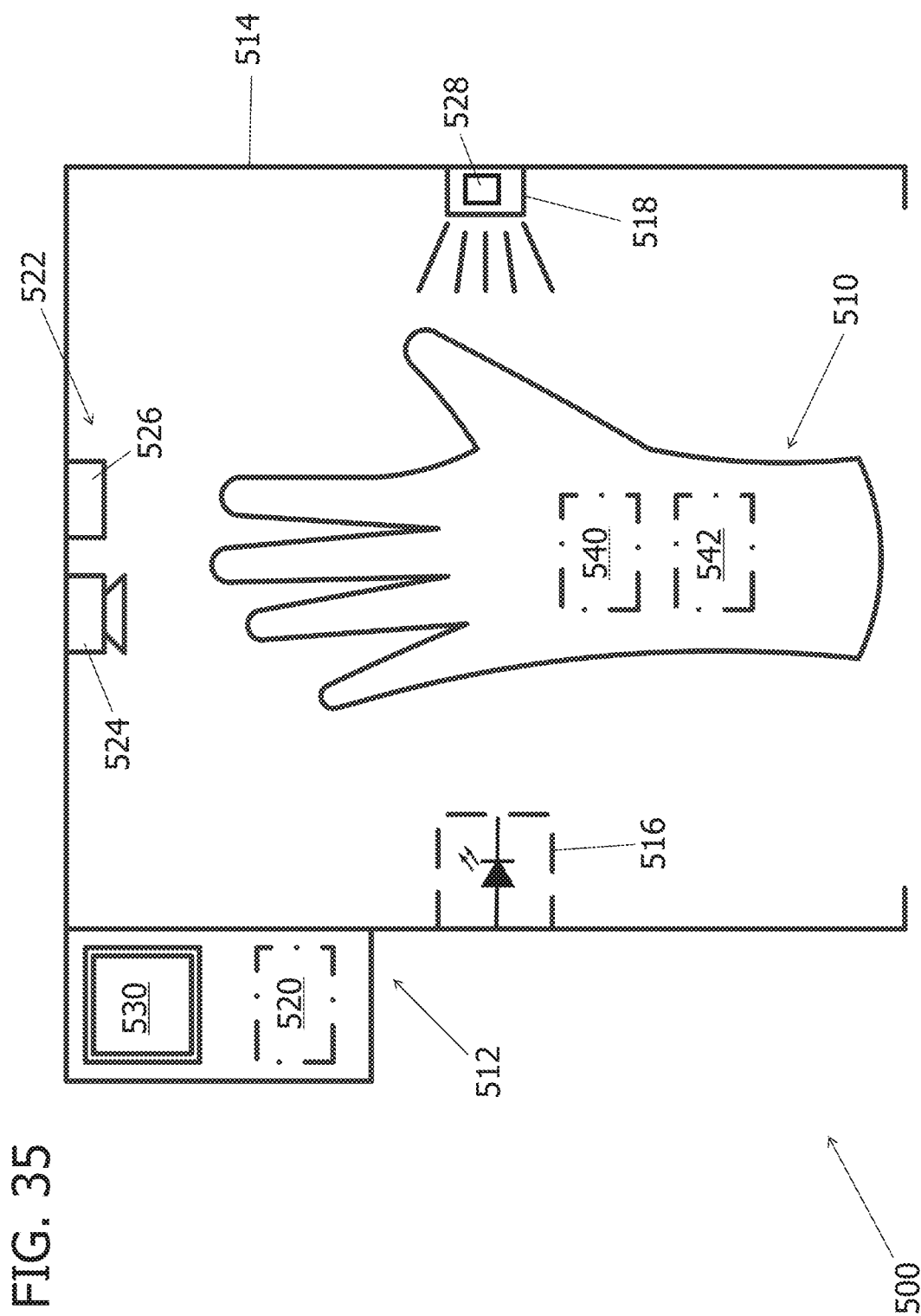
FIG. 35 is a schematic illustration of a sterilization system.

Referring to FIG. 35, one embodiment of a system for treating multiple patients without disrobing is generally indicated at reference number 500. The system 500 includes a garment, generally indicated at 510, and a sterilization device, generally indicated at 512. The sterilization device 512 comprises a sterilization chamber 514 having an opening and an interior. The chamber 514 is sized and arranged so the garment 510 can pass through the opening into the interior while the garment is donned by an individual such as a medical practitioner. It is understood that that chamber 514 can be sized for simultaneously receiving multiple garments (e.g., two gloves) therein.

One or more sterilizers 516, 518 are mounted on the sterilization chamber 514 to provide a sterilization input to the garment 510 received in the chamber. In the illustrated embodiment the sterilizer 516 comprises an electromagnetic radiation source that generates a sterilization input comprising electromagnetic radiation configured to sterilize the garment (e.g., UVC radiation). The sterilizer 518 comprises a fluid dispenser configured to dispense a sterilization fluid (e.g., alcohol, etc.) onto the garment. It will be understood that other sterilizers can be used in other embodiments. In addition, it is understood that the sterilization device 512 can include any number of radiation sources, fluid dispensers, and/or other sterilizers. In certain embodiments, the electromagnetic radiation source 516 can comprise one or more LEDs, such as one or more UVC LEDs. For example one or more LEDs (or other radiation source) can be arranged at spaced apart locations on the chamber 514 to direct sterilizing radiation to the entire exterior surface of the garment 510 received in the chamber. Similarly, sterilization fluid dispensers 518 can be arranged at spaced apart locations on the chamber 514 to direct sterilization fluid to the entire exterior surface of the garment 510. In other embodiments, one or more of the sterilizers 516, 518 can be mounted on a carriage that is configured to move the sterilizer(s) 360° about the garment 510 received in the chamber 514. The sterilizers 516, 518 can continuously (or intermittently) sterilize the garment as they are driven 360° around the perimeter of the garment to sterilize the entire garment.

In the illustrated embodiment, the sterilization device 510 includes a controller 520 that is configured to automatically control the sterilizers 516, 518 based on a preprogrammed control routine to fully sterilize the garment 510. In one or more embodiments, the control routine can be a time-based control routine such that the controller 520 controls the radiation source 516 and/or fluid dispenser 518 to direct sterilizing radiation and/or fluid to the garment 510 for a predetermined amount of time. In certain embodiments, the controller 520 can direct a carriage (not shown) to move the sterilizers 516, 518 through one or more complete, 360° revolutions about the garment 510 to fully sterilize the garment.

In the illustrated embodiment, the sterilization device 512 includes a sensing system 522 configured to generate one or more signals representative of an amount of sterilizing radiation and/or fluid (and/or other sterilization input) that is applied to the garment 510. The controller 520 is configured to receive the signal(s) from the sensing system 522 and control the radiation source 516 and/or fluid dispenser 518 based on the signal(s). The illustrated sensing system 522 includes the following sensors: a garment camera 524 (broadly, a garment detector) that is configured to generate a signal from which the controller 520 can determine a position of the garment 510 in the chamber 514; an electromagnetic radiation sensor 526 that is configured to transmit a signal to the controller representative of the electromagnetic radiation generated by the radiation source 516 (in certain embodiments, the controller can also receive similar information by monitoring the power consumed by the electromagnetic radiation source); and a flow sensor 528 (broadly, a fluid sensor) configured to transmit a signal to the controller representative of sterilization fluid that is dispensed by the dispenser 518 (other fluid sensors configured to detect the sterilization fluid that is dispensed and/or delivered to the garment can also be used in other embodiments).

The controller 520 is configured to use the signals from the sensors 524, 526, 528 to determine how much of the sterilization radiation and sterilization fluid (broadly, sterilization inputs) is imparted on the garment 510. For example, in one embodiment, the controller 520 is configured to conduct a synchronized comparison of the signal provided by the garment detector 524 (which provides an indication of when the garment is operatively aligned with the sterilizers 516, 518) and the signals provided by the radiation sensor 526 and the fluid sensor 528 (which provide indications of the amount of sterilization inputs that are generated by the sterilizers). Based on the synchronized comparison, the controller 520 determines when enough sterilizing input has been imparted on the garment 510 to sterilize the garment. It will be understood that the controller could determine sterilization progress in other ways in other embodiments. When the controller 520 determines that the garment is sterilized, it generates a sterilization indication on an indicator 530 (e.g., a display, a loudspeaker, etc.), which is mounted on the chamber 514 in the illustrated embodiment. In other embodiments, the sterilization indication can be provided by haptic feedback to the user donning the garment as explained below. The controller can also send a signal to a remote or nearby device (e.g., a mobile device (phone or tablet), a computer or server, etc.) that causes the other device to provide the sterilization indication and/or store data related to the sterilization that took place.

In the illustrated embodiment, the garment 510 comprises a glove. However, other types of garments—e.g., an apron, a vest, a gown, a shirt, a sleeve, pants, coveralls, a hat, a facemask, etc.—can also be used without departing from the scope of the invention. In one or more embodiments, the glove 510 is formed from the material 200 described above. For example, the glove 510 can include an inner, UV-opaque liner and an impermeable outer layer that is configured to be sterilized by UVC radiation.

The glove 510 is configured for data communication with the sterilization device 512 such that the system 500 uses the glove and the sterilization device in combination to control a sterilization routine. In the illustrated embodiment, the glove 510 is configured for a wireless data connection with the sterilization device 512, but other embodiments could instead have a wired connection.

The glove 510 includes one or more radiation sensors 540 (broadly, sterilization input sensor) that are configured to detect UVC radiation (broadly, a sterilization input) imparted on the glove. The sensor 540 generates a signal representative of the UVC radiation that is received by the glove 510 and transmits the signal to the controller 520. The controller 520 can use the signal from the sensor 540 (either alone or in combination with other signals, e.g., signals from the sensors 524, 526, 528) to determine when the sterilization device 512 has imparted enough UVC radiation onto the glove 510 to sterilize the glove. It will be understood that the glove can also include other sterilization input sensors (e.g., fluid sensors, etc.) that are configured to detect when other types of sterilization inputs provided by the sterilization device 512 are imparted on the glove 510.

As explained above, when the controller 520 determines that the glove 510 has been sterilized, it can provide the person wearing the glove an indication that sterilization is complete. In the illustrated embodiment, the glove 510 includes one or more vibrators 542 (broadly, haptic feedback indicators) that are configured to provide haptic feedback directly to the hand donning the glove. Thus, when the controller 520 determines that the glove 510 has been sterilized, it provides an output signal (e.g., a wireless output signal) to the glove that causes the vibrator 542 to vibrate a portion of the glove. The user can feel the vibration and is thereby notified through haptic feedback that sterilization is complete.

Physical activity requires proper muscle activation sequencing. For example, high performing athletes activate and relax muscles in consistent sequences to carry out repetitive motions. In addition, lay people activate and relax muscles in normal sequences to carry out mundane motions such as walking, running, etc. To improve the quality of motions—for example, in order to undertake athletic training at a high level or to reeducate muscles after trauma through injury, loss of limb, surgery, stroke, etc.—physical therapists and other trainers have attempted to teach muscle sequencing through visualization. A subject watches video that demonstrates desirable muscle activation sequencing and attempts to replicate what was shown using their own muscles. However, it can be difficult for a subject to effectively replicate the proper sequencing through volitional activation and relaxation of the muscles alone.

Figure 33:
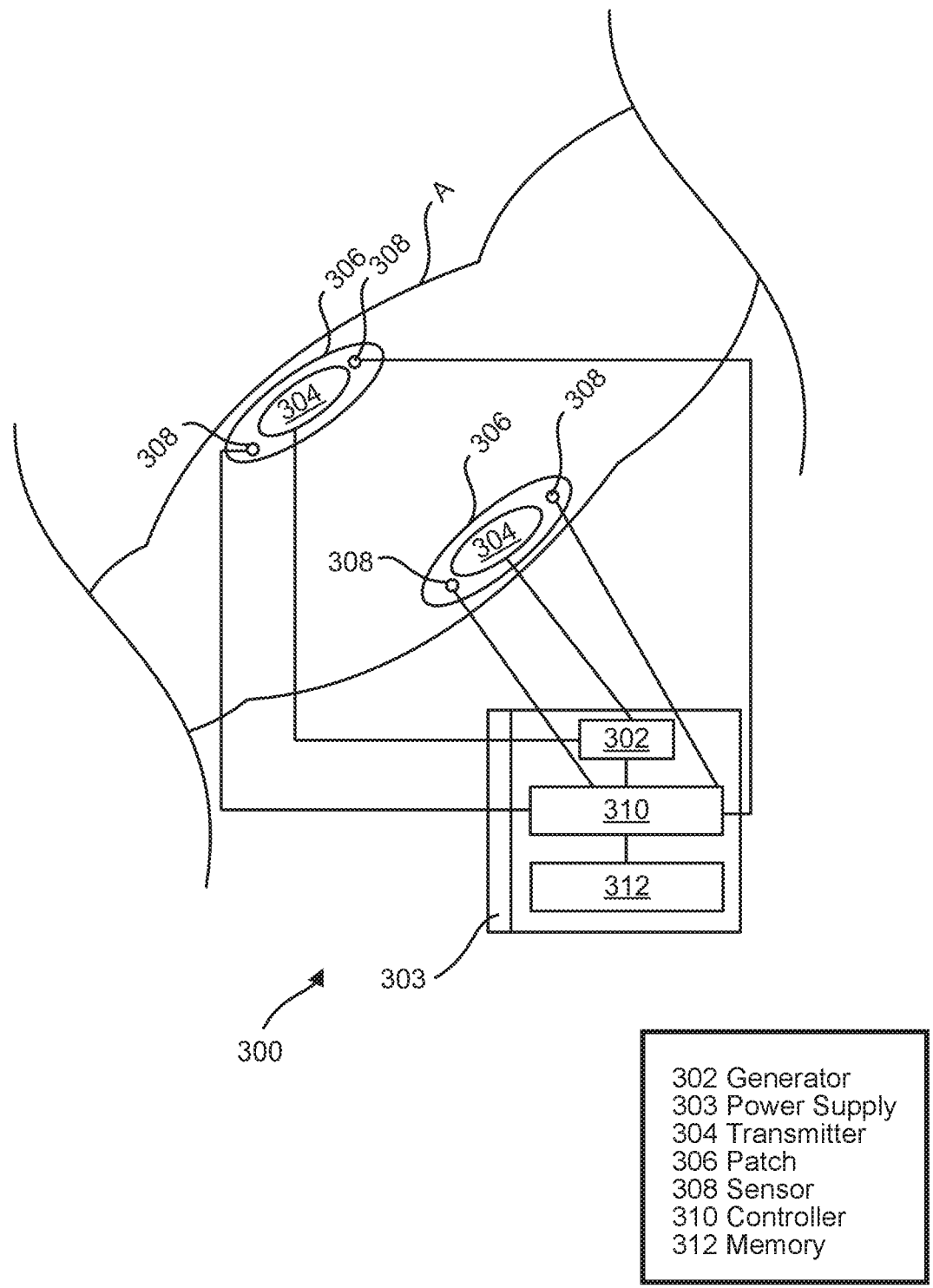
FIG. 33 is a schematic illustration of a sequential muscle activation system operatively connected to an arm of a subject.
Figure 34:
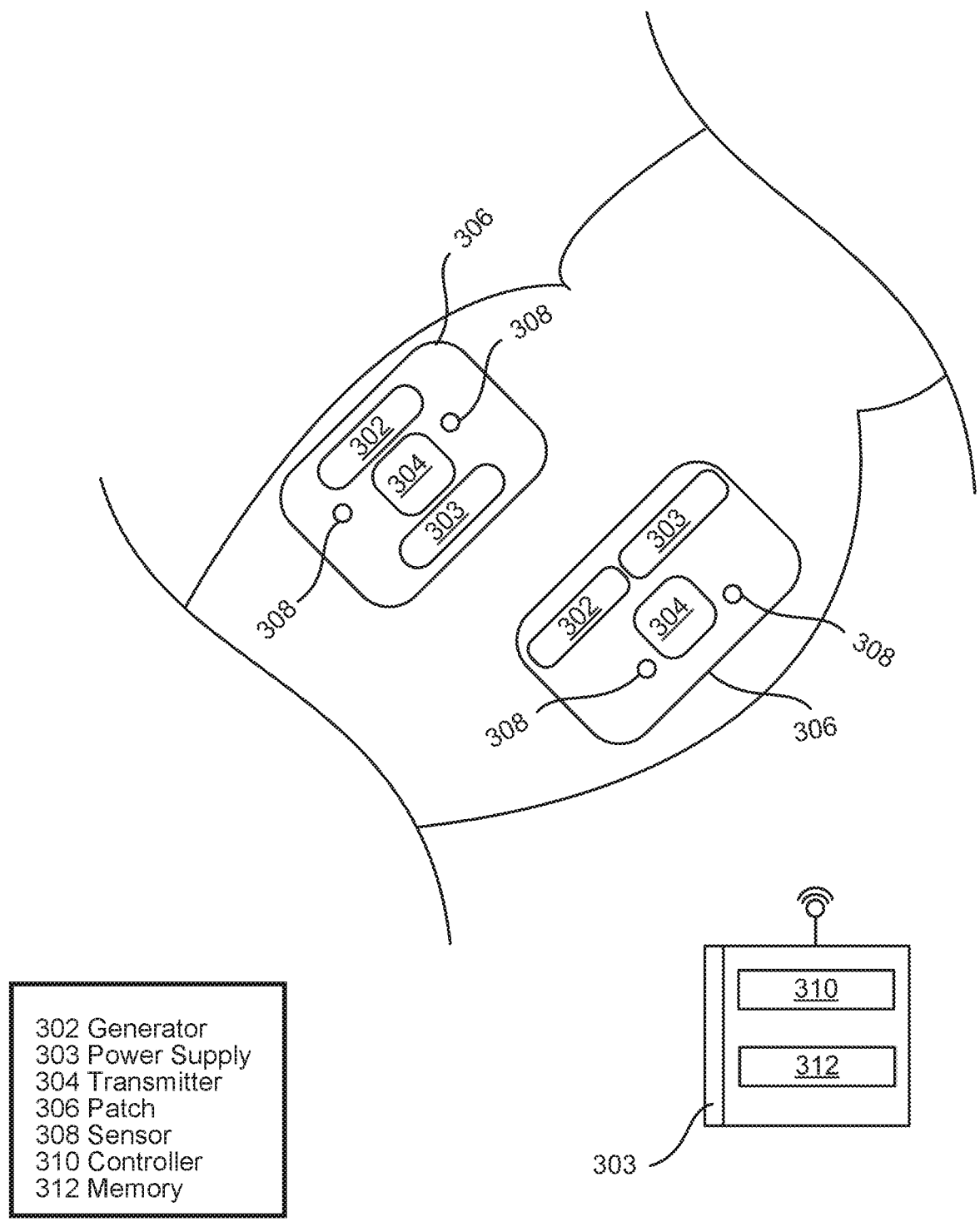
FIG. 34 is a schematic illustration of another embodiment of a sequential muscle activation system operatively connected to an arm of a subject.

Referring to FIG. 33, one embodiment of a sequential muscle activation system is generally indicated at reference number 300. The muscle activation system 300 includes a stimulation generator 302 that is configured to generate one or more muscle activation stimuli that are configured to selectively activate and relax the muscles of the subject. In the illustrated embodiment, the stimulation generator 302 is configured to draw power from a power supply 303 such as a battery. A plurality of stimulation transmitters 304 are operatively connected to the stimulation generator 304 to transmit the muscle activation stimuli to respective muscles of the subject. The transmitters 304 are mounted on patches 306 that are temporarily adhered to the arm A of the subject. It is also contemplated that the transmitters and/or generators could be mounted on any of the handles or gloves described above, for example. The transmitters 304 are connected to the generator 302 through respective wired connections, but in other embodiments transmitters can be connected to the generator in other ways (e.g., wireless connection, by being mounted directly on the generator, by being mounted together with the generator 302 and a patch power supply 303 on a respective patch 306 as shown in FIG. 34, etc.). It is also understood that separate generators can be used for each transmitter in other embodiments (e.g., as shown in FIG. 34). In the configuration illustrated in FIG. 33, one patch 306 extends over the biceps of the subject and the other patch extends over the triceps of the subject. In this configuration, the transmitters 304 are configured to transmit the stimuli to the biceps and triceps of the subject arm A, respectively. It is understood that the transmitters 304 of sequential muscle activation system 300 could be operatively connected to other muscles of the subject in other embodiments. Likewise, it is understood that more than two transmitters may be used with the muscle activation system in other embodiments.

The muscle activation system 300 can be configured to transmit any suitable type of stimulus for selectively activating and relaxing the muscles. In one or more embodiments, the generator 302 is configured to generate a noxious stimulus that is transmitted through the transmitters 304 to the subject. Examples of suitable noxious stimuli include electrical stimuli (e.g., TENS, Russian stimulation, etc.), thermal stimulation (heat stimulation, cold stimulation), mechanical stimulation (vibration, etc.), optical stimulation (e.g., laser energy, etc.), etc. In some embodiments, the sequential muscle activation system 300 includes one or more generators 302 configured to generate multiple types of stimulation. In other embodiments, the system 300 can include one or more generators configured to generate a single type of stimulus.

The sequential muscle activation system 300 further includes sensors 308 configured to sense a response of the subject to the muscle activation stimuli. In the illustrated embodiment, the sensors 308 are mounted on the patches 306 for operative connection with the respective muscles of the subject. In one or more embodiments, the sensors 308 can comprise muscle stretch sensors, motion sensors, ultrasound sensors, etc. In some embodiments, the sensors can include cameras or other sensors that are spaced apart from the subject to sense the response of the subject to the muscle activation stimuli.

The muscle activation system 300 further includes a controller 310 that is operatively connected to the stimulation generator 302 to selectively direct a muscle activation stimulus from the generator to each of the stimulation transmitters 304 to transmit muscle activation signals to the respective muscles of the subject. The controller 310 can be operatively connected to the stimulation generator 302 and the transmitters 304 in any suitable fashion (e.g., by a wired connection as shown in FIG. 33 or a wireless connection as shown in FIG. 34). Suitably, the controller 310 is configured to execute a control routine using the stimulation generator 302 and the stimulation transmitters 304 that sequentially activates and relaxes the muscles to which the transmitters are connected in a desired muscle activation sequence. In general, the controller 310 can be configured to control the timing at which a stimulus is conveyed to the muscles of the subject (e.g., the start time and period of a stimulus) in accordance with a desired muscle activation sequence. For example the controller 310 can be configured to execute certain control routines that are configured to activate or fire the muscles for very short increments of time (e.g., on the order of fractions of a second or fractions of a millisecond, etc.). In some embodiments, the controller is configured to control which types of stimuli are conveyed at a given time and/or to selectively adjust an intensity of a stimuli. In the illustrated embodiment, the controller 310 is operatively connected to a memory 312 configured to store one or more control routines including data representative of a desired muscle activation sequence. In one embodiment, the desired muscle activation sequence is determined using a recording system (not shown) that records the muscle activation sequence of an exemplary individual (e.g., an able-bodied individual, a high performing athlete, etc.) and stores a control routine on the memory 312 that, when executed by the controller 310, selectively activates and relaxes the muscles of the subject in the muscle activation sequence recorded from the exemplary individual.

In the illustrated embodiment, the controller 310 is operatively connected to the muscle response sensors 308 to receive muscle response signals from the sensors. In one embodiment, the controller 310 stores the muscle response signals from the sensors 308 in the memory 312 for use in diagnosing, training, and evaluating the subject. In additional embodiments, the controller 310 is configured to use the muscle response signals to control the stimulation generator 302 and the stimulation transmitters 304. For example, in some embodiments, the controller 310 can be configured to only impart a stimulus to a muscle when signal from the sensor indicates that the muscle is not activating or relaxing in accordance with a desired muscle activation sequence. Thus, when the muscles of the subject are activating out of sequence, the controller 310 selectively conveys stimuli from the generator 302 through the transmitters 304 to correct the activation sequencing of the muscles. In one embodiment, the muscle response sensors 308 are used to detect and record the muscle activation sequence of one or more athletes to determine a desired muscle activation sequence for training a subject. The muscle activation sequence of the athlete detected by the sensors 308 is stored in the memory 312 to establish a control routine used by the controller to selectively activate the muscles of the subject in the desired sequence. Various additional data about the subject may be determined using other patient monitoring techniques and such data may be fed back to the controller 310 to use in controlling the muscle activation sequence. Exemplary patient monitoring techniques are disclosed in U.S. Pat. No. 7,182,738, U.S. Patent Application Publication No. 2007/0135738, U.S. Patent Application Publication No. 2013/0274653, U.S. Patent Application Publication No. 2014/0276237, U.S. Patent Application Publication No. 2014/0171809, and U.S. Patent Application Publication No. 2015/0327778, each of which is expressly incorporated by reference in its entirety for all purposes.

The sequential muscle activation system 300 can be used to train various muscle groups to fire in various muscle activation sequences. For example, in one embodiment, the muscle activation system 300 is configured to selectively activate and relax an agonist muscle and a corresponding antagonist muscle in alternating sequence. In some embodiments, the muscle activation system 300 can be configured to selectively activate and relax muscles used in a particular athletic technique in accordance with a desired muscle activation sequence. For example, the muscle activation system 300 can be configured to selectively activate and relax muscles used to train an athlete in, for example, tennis to perform a backhand stroke, a forehand stroke, a serve, impart certain spins on a ball, etc.; baseball to perform certain pitches or swing strokes, etc. (e.g., the muscle activation system 300 could be used to train pitchers to perform pitches using muscle activation sequences that limit stresses imparted on the ulnar collateral ligament or pronator group, etc.); in golf to swing a driver, an iron, a putter, etc.; and in other sports for other techniques. The specific muscle activation sequences directed by the system 300 may be based on the recorded muscle activation sequences of high performing athletes in the same sports. In another embodiment, the muscle activation system is used to train a high-skill fine motor movement, such as surgical technique. In still other embodiments, the muscle activation system 300 is configured to selectively activate and relax muscles in a desired muscle activation sequence to reeducate the muscles of the subject to perform mundane or common tasks after injury or trauma. For example, after an injury, stroke, muscular distrophy, etc., the muscle activation system 300 can selectively activate and relax certain muscles of subject in accordance with a desired muscle activation sequence to retrain the subject in walking (e.g., the muscle activation system can be operatively connected to the thigh, calf, hamstrings, quadriceps, abductor/adductor of the gluteus, etc. to retrain a normal walking gait) or other gross motor skills or to retrain the subject in various fine motor skills such as eating, writing, typing, etc.

In one embodiment, the muscle activation system 300 is used in combination with a body-controlled robotic prosthetic limb. For example, it is known in the art to operatively connect a prosthetic limb to a subject comprising robotically movable parts that are controllable based on muscle activation. The muscle activation system 300 can be used to train a muscle activation sequence that controls a robotic prosthetic in a manner that simulates the pattern of motion of a natural limb. More specifically, the patch 306 can be placed on the stump of the subject at or adjacent the location where the prosthetic is configured to be controlled by activation of the subject's muscles. Stimuli from the generator 302 are transmitted through the transmitter 304 to the subject muscles to train the subject muscles for using the robotic prosthetic. For example, the activation system 300 can stimulate the muscles to train the muscles to have the necessary endurance for using the prosthetic (e.g., by periodically (e.g., daily, weekly, multiple-times weekly, etc.) stimulating the muscles in predefined muscle activation sequence over the course of an endurance training period, such as an endurance training period extending at least about two weeks, at least about one month, at least about two months, at least about three months, at least about four months, at least about five months, at least about six months, at least about nine months, at least about twelve months, at least about 18 months, at least about 24 months, etc.). In addition, the activation system 300 can stimulate the muscles to train a muscle activation sequence that will direct the robotic prosthetic to perform certain tasks.

In another embodiment, the muscle activation system 300 could be used in combination with a robotic exoskeleton in a similar manner to how the system is described as being used in combination with a robotic prosthetic above.

Modifications and variations of the disclosed embodiments are possible without departing from the scope of the invention defined in the appended claims.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

The invention claimed is:

1. A method of training a body part, the method comprising:
    coupling a muscle stimulus generator to the body part, wherein the muscle stimulus generator is configured to generate a muscle activation stimulus and a muscle relaxation stimulus;
    generating a muscle activation stimulus and a muscle relaxation stimulus using the generator, wherein the step of generating the muscle activation stimulus and the muscle relaxation stimulus comprises generating an alternating sequence of muscle activation stimuli and muscle relaxation stimuli; and
    transmitting the generated alternating sequence of muscle activation stimuli and muscle relaxation stimuli to an agonist muscle and a corresponding antagonist muscle, respectively, of the body part to alternatingly i) activate the agonist muscle and relax the antagonist muscle and ii) relax the agonist muscle and activate the antagonist muscle.

2. A method as set forth in claim 1, wherein the step of generating the muscle activation stimulus and the muscle relaxation stimulus comprises sending programmed control instructions to the muscle stimulus generator.

3. A method as set forth in claim 2, wherein the programmed control instructions are configured to control the muscle stimulus generator to generate a predefined muscle activation stimulus and a predefined muscle relation stimulus.

4. A method as set forth in claim 3, wherein the step of transmitting the muscle activation stimulus to the agonist muscle and the muscle relaxation stimulus to the antagonist muscle activates the agonist muscle and relaxes the antagonist muscle to move the body part in a specified movement.

5. A method as set forth in claim 2, further comprising recording a muscle activation sequence of another body part while performing a specified movement.

6. A method as set forth in claim 5, further comprising programming the control instructions based on the recorded muscle activation sequence.

7. A method as set forth in claim 1, wherein said generating the muscle activation stimulus comprises generating a noxious stimulus.

8. A method as set forth in claim 1, wherein the step of generating the muscle activation stimulus and the muscle relaxation stimulus comprises generating at least one of an electrical stimulus, a thermal stimulus, an optical stimulus, and a mechanical stimulus.

9. A method as set forth in claim 1, wherein the step of transmitting the generated muscle activation stimulus and muscle relaxation stimulus comprises at least one of imparting TENS to the body part, imparting Russian stimulation to the body part, heating the body part, vibrating the body part, and imparting laser energy to the body part.

10. A method as set forth in claim 1, further comprising sensing a response of the body part to the transmitted muscle activation stimulus and muscle relation stimulus.

11. A method as set forth in claim 10, wherein the step of sensing the response of the body part comprises sensing the response of the body part using one of a muscle stretch sensor, a motion sensor, an ultrasound sensor, and a camera.

12. A method as set forth in claim 10, further comprising adjusting at least one of the muscle activation stimulus and the muscle relaxation stimulus based on the sensed response of the body part.

13. A method as set forth in claim 1, wherein the body part comprises a stump and wherein the step of transmitting the generated muscle activation stimulus and muscle relaxation stimulus causes the stump to perform a movement configured to control a robotic prosthetic limb.

14. A method as set forth in claim 1, further comprising periodically repeating the steps of generating and transmitting the muscle activation stimulus and muscle relaxation stimulus over a period of at least two weeks to train muscle memory.

15. A method as set forth in claim 1, wherein the step of coupling a muscle stimulus generator to the body part comprises attaching a muscle activation stimulus transmitter to the body part, the muscle activation stimulus transmitter being configured to transmit the generated muscle activation stimulus to the muscle during the transmitting step.

16. A method as set forth in claim 15, wherein the step of attaching the muscle activation stimulus transmitter to the body part comprises securing a patch to the body part.

17. A method as set forth in claim 16, wherein by the step of securing the patch, at least one of the following steps is also performed:
    connecting a body part sensor to the body part;
    mounting the muscle stimulus generator on the body part; and
    mounting a power supply on the body part.

18. A muscle activation system comprising;
    a stimulation generator configured to generate a muscle activation stimulus and a muscle relaxation stimulus;
    a plurality of stimulation transmitters operatively connected to the stimulation generator and configured to transmit the muscle activation stimulus and the muscle relaxation stimulus from the stimulation generator to respective muscles of a subject; and
    a controller configured to control the generator to generate an alternating sequence of muscle activation stimuli and muscle relaxation stimuli;
    wherein the stimulation transmitters are configured to transmit the predefined sequence of muscle activation stimuli and muscle relaxation stimuli to an agonist muscle and a corresponding antagonist muscle, respectively, of the body part to alternatingly i) activate the agonist muscle and relax the antagonist muscle and ii) relax the agonist muscle and activate the antagonist muscle.

* * * * *